US008143413B2

(12) United States Patent
Dewa et al.

(10) Patent No.: US 8,143,413 B2
(45) Date of Patent: Mar. 27, 2012

(54) POLYCATIONIZED PHOSPHOLIPID DERIVATIVES

(75) Inventors: Takehisa Dewa, Aichi (JP); Tomohiro Asai, Shizuoka (JP); Mamoru Nango, Aichi (JP); Naoto Oku, Shizuoka (JP)

(73) Assignees: Eisai R&D Management Co., Ltd., Tokyo (JP); National University Corporation Nagoya Institute of Technology, Nagoya, Aichi (JP); Shizuoka Prefectural Universities Corporation, Shizuoka-Shi (JP)

( * ) Notice: Subject to any disclaimer, the term of this patent is extended or adjusted under 35 U.S.C. 154(b) by 0 days.

(21) Appl. No.: 12/550,196

(22) Filed: Aug. 28, 2009

(65) Prior Publication Data

US 2010/0094020 A1 Apr. 15, 2010

Related U.S. Application Data

(60) Provisional application No. 61/093,518, filed on Sep. 2, 2008.

(51) Int. Cl.
*C07F 9/06* (2006.01)
*C07F 9/02* (2006.01)
*C07C 69/34* (2006.01)
(52) U.S. Cl. ............................ 548/112; 560/195; 564/12
(58) Field of Classification Search ........................ None
See application file for complete search history.

(56) References Cited

U.S. PATENT DOCUMENTS

| 3,654,300 A | 4/1972 | Redmore |
| 2007/0059353 A1 | 3/2007 | Harashima et al. |

FOREIGN PATENT DOCUMENTS

| EP | 1046394 A2 | 10/2000 |
| EP | 1854807 A1 | 11/2007 |
| GB | 1299954 A | 12/1972 |
| JP | 48-17264 B | 5/1973 |
| JP | 2003-530875 A | 10/2003 |
| JP | 2005-247750 A | 9/2005 |
| JP | 2005-247751 A | 9/2005 |
| JP | 2007-166946 A | 7/2007 |
| WO | WO 01/81408 A2 | 11/2001 |
| WO | WO 2005/032593 A1 | 4/2005 |
| WO | WO 2006/088245 A1 | 8/2006 |

OTHER PUBLICATIONS

Dewa et al., caplus an 2004:453679.*
Asai et al., "Angiogenic vessel-targeted liposomal DDS for cancer treatment," 11th Liposome Research Days Conference, Yokohama, Japan, Jul. 20, 2008, 19 slides.
Asai et al., "Angiogenic vessel-targeted liposomal DDS for cancer treatment," 11th Liposome Research Days Conference, Yokohama, Japan, Jul. 21, 2008, Abstract.
Asai et al., "Angiogenic vessel-targeted liposomes for in vivo delivery of siRNA," Japan Society of Gene Therapy, The 14th Annual Meeting 2008, Sapporo, Japan, Jun. 14, 2008, Abstract, 38 slides.
Asai et al., "Disappearance of the angiogenic potential of endothelial cells caused by Argonaute2 knockdown," Biochemical and Biophysical Research Communications, vol. 368, 2008, pp. 243-248.
Baba et al., "Development of novel polycationic lipids for a gene carrier: morphology changes of their DNA complexes and their functions," 57th Symposium Macromolecules, Shizuoka, Japan, Sep. 26, 2008, 20 slides and English translation.
Berlin et al., "Arenesulfonyl imidazolides, new reagents for polynucleotide synthesis," Tetrahedron Letters No., vol. 14, 1973, pp. 1353-1354.
Blume et al., "Liposomes for the sustained drug release in vivo," Biochimica et Biophysica Acta, vol. 1029, 1990, pp. 91-97.
Deamer et al., "Large volume liposomes by an ether vaporization method," BBA Report, BBA 71267, Biochimica et Biophysica Acta, vol. 443, 1976, pp. 629-634.
Dewa et al., "Novel polyamine-dialkyl phosphate conjugates for gene carriers. Facile synthetic route via an unprecedented dialkyl phosphate," Bioconjugate Chem., 2004, vol. 15, No. 4, pp. 824-830.
Eibl et al., "The influence of charge on phosphatidic acid bilayer membranes," Biochimica et Biophysica Acta, vol. 553, 1979, pp. 476-488.
Enoch et al., "Formation and properties of 1000-Å-diameter, single-bilayer phospholipid vesicles," Proc. Natl. Acad. Sci., vol. 76, No. 1, Jan. 1979, pp. 145-149.
Futaki et al., "Arginine-rich peptides, an abundant source of membrane-permeable peptides having potential as carriers for intracellular protein delivery," The Journal of Biological Chemistry, vol. 276, No. 8, Feb. 23, 2001, pp. 5836-5840.
Futaki, et al. "Stearylated arginine-rich peptides: a new class of transfection systems," Bioconjugate Chem., 2001, vol. 12, pp. 1005-1011.
Hatanaka et al., "Construction of siRNA Delivery System Targeting to Angiogenesis Vessels with Peptide-Modified Liposomes," The 128th Annual Meeting of the Pharmaceutical Society of Japan, Yokohama, Japan, Mar. 27, 2008, 24 slides, Abstract and English translation of Abstract.
Hattori et al., "Poly(2-methyl-N6-methyladenylic acid): synthesis, properties, and interaction with poly(uridylic acid)," Biochemistry, vol. 13, No. 13, 1974, pp. 2754-2761.
Kato, "Current status of the studies on the instrumentation for LB deposition and on the structure of LB films," Oil Chemistry, vol. 39, 1990, pp. 141-147.
Kenjo et al., "Development of liposomal siRNA targeting tumor angiogenic vessels," 11th Liposome Research Days Conference, Yokohama, Japan, Jul. 21, 2008, 3 slides, abstract and poster.
Khalil et al., "High density of octaarginine stimulates macropinocytosis leading to efficient intracellular trafficking for gene expression," The Journal of Biological Chemistry, vol. 281, No. 6, Feb. 10, 2006, pp. 3544-3551.
Klibanov et al., "Amphipathic polyethyleneglycols effectively prolong the circulation time of liposomes," FEBS Letters, vol. 268, No. 1, Jul. 1990, pp. 235-237.

(Continued)

*Primary Examiner* — Sun Jae Loewe
(74) *Attorney, Agent, or Firm* — Birch, Stewart, Kolasch & Birch, LLP

(57) ABSTRACT

The present invention provides novel phospholipid derivatives. Furthermore, the present invention provides lipid membrane structures excellent in gene/nucleic acid introduction efficiency into a cell.

13 Claims, 4 Drawing Sheets

OTHER PUBLICATIONS

Kobayashi et al., "Synthesis and functional evaluation of polycationic lipids for gene carrier," 56th Symposium on Macromolecules, Nagoya, Japan, Polymer Preprints, vol. 56, No. 2, Sep. 21, 2007, p. 5091, English translation, two sets of 10 slides and two sets of English translations of slides.

Matsuoka et al., "The use of liposomes to study COPII- and COPI-coated vesicle formation and membrane protein sorting," Methods, vol. 20, 2000, pp. 417-428.

Matsushita et al., "Antiangiogenic effect by Argonaute2 knockdown used polycation liposome," 11th Liposome Research Days Conference, Yokohama, Japan, Jul. 21, 2008, Poster, 3 slides and Abstract.

Matsushita et al., "Development of angiogenic vessel-targeted polycation liposomes for delivering small interfering RNA," 35th Annual Meeting & Exposition of the Controlled Release Society, New York, USA, Jul. 16, 2008, Abstract (2 pages), Poster (2 pages).

Matsuura et al., "Polycation liposome-mediated gene transfer in vivo," Biochimica et Biophysica Acta, vol. 1612, 2003, pp. 136-143.

Mishiro et al., "Construction of gene delivery system using novel siRNA carrying technology," The 128th Annual Meeting of the Pharmaceutical Society of Japan, Yokohama, Japan, Mar. 26, 2008, 14 slides, English translation of slides, Abstract and English Translation of Abstract.

Mizuno et al., "New phosphorylation procedure. Activation of phosphates with cyclohexyl isocyanide," J.C.S. Chem. Comm., 1974, pp. 997-998.

Niwada et al., "Effect of polyamine structure on transfection efficiency in gene transfection using polycation liposomes," The 23rd Annual Meeting of the Academy of Pharmaceutical Science and Technology, Sapporo, Japan, May 20, 2008, 10 slides with English translation, Abstract and English translation of Abstract.

Niwada et al., "Effect of Polyamine Structure on Transfection efficiency in polycation liposome transfection method," Meeting of Tokai Branch, Pharmaceutical Society of Japan, Shizuoka, Japan, Dec. 6, 2008, 10 slides, English translation of first slide, Abstract in Japanese and English.

Niwata et al., "Development of novel polycation liposomes for gene transfer system," 35th Annual Meeting & Exposition of the Controlled Release Society, Jul. 16, 2008, Article (2 pages), Poster (2 pages).

Oku et al., "A novel non-viral gene transfer system, polycation liposomes," Advanced Drug Delivery Reviews, vol. 52, 2001, pp. 209-218.

Oku et al., "Anti-neovascular therapy using novel peptides homing to angiogenic vessels, " Oncogene, 2002, vol. 21, pp. 2662-2669.

Pick, "Liposomes with a large trapping capacity prepared by freezing and thawing of sonicated phospholipid mixtures," Archives of Biochemistry and Biophysics, vol. 212, No. 1, Nov. 1981, pp. 186-194.

Sugiyama et al., "Possible mechanism of polycation liposome (PCL)-mediated gene transfer," Biochimica et Biophysica Acta, vol. 1660, 2004, pp. 24-30.

Szoka, Jr. et al., "Comparative properties and methods of preparation of lipid vesicles (liposomes)," Ann. Rev. Biophys. Bioeng., 1980, vol. 9, pp. 467-508.

Szoka, Jr. et al., "Procedure for preparation of liposomes with large internal aqueous space and high capture by reverse-phase evaporation," Proc. Natl. Acad. Sci., vol. 75, No. 9, Sep. 1978, pp. 4194-4198.

Uchida et al., "Functional evaluation of polycationic lipids as gene carriers," 57th Symposium on Macromolecules, Schizuoka, Japan, Sep. 26, 2008, 17 slides.

Uchida et al., "Synthesis and functional evaluation of liposomal polycationic lipids for gene transfer," 11th Liposome Research Days Conference, Yokohama, Japan, Jul. 21, 2008, 11 slides.

Ueno et al., "Synthesis and silencing properties of siRNAs possessing lipophilic groups at their 3'-termini," Bioorganic & Medicinal Chemistry, vol. 16, 2008, pp. 7698-7704.

von Tigerstrom et al., "Preparation of the 2,4-dinitrophenyl esters of thymidine 3'- and thymidine 5'-phosphate and their use as substrates for phosphodiesterases," Biochemistry, vol. 8, No. 7, Jul. 1969, pp. 3067-3070.

Wheeler et al., "Stabilized plasmid-lipid particles: construction and characterization," Gene Therapy, 1999, vol. 6, pp. 271-281.

Yamazaki et al., "Polycation liposomes, a novel nonviral gene transfer system, constructed from cetylated polyethylenimine," Gene Therapy, 2000, vol. 7, pp. 1148-1155.

Yokota et al., "Development of anticancer therapy based on mTOR knockdown," Meeting of Tokai Branch, Pharmaceutical Society of Japan, Gifu, Japan, Dec. 8, 2007, 10 slides and English translation of slides, Abstract and English translation of Abstract.

International Search Report including Forms PCT/ISA/220, PCT/ISA/210 and PCT/ISA/237 for corresponding International Application No. PCT/JP2008/065744 mailed Nov. 18, 2008.

Dewa et al., "Liposomal polyamine-dialkyl phosphate conjugates as effective gene carriers: chemical structure, morphology, and gene transfer activity," Bioconjug Chem, May 19, 2010, vol. 21, No. 5, pp. 844-852.

Tsuzuku et al., "Development of in vivo delivery for siRNA-based cancer therapy," Oral presentation at 31st Symposium on Biomembrane-Drug Interaction held at Osaka University Convention Center, 2009, Abstract.

Asai et al., "Dicetyl Phosphate-tetraethylene-pentamine-based liposomes for systemic siRNA delivery," Bioconjugate Chemistry, Mar. 16, 2011, vol. 22, No. 3, pp. 429-435, epublished Mar. 1, 2011.

* cited by examiner

POLYCATIONIZED PHOSPHOLIPID DERIVATIVES

This application claims priority to provisional U.S. Application Ser. No. 61/093,518, filed Sep. 2, 2008, herein incorporated by reference.

FIELD OF THE INVENTION

The present invention relates to novel phospholipid derivatives. More specifically, the present invention relates to phospholipid derivatives useful for producing lipid membrane structures (a liposome, an emulsion and a micelle and the like) in which medicinal ingredients such as a gene and a nucleic acid are to be encapsulated. Furthermore, the present invention relates to lipid membrane structures, useful as a therapeutic carrier and a laboratory reagent, that can introduce, e.g., a gene and a nucleic acid having high gene expression efficiency and a high gene expression suppression effect into a cell.

BACKGROUND OF THE INVENTION

In treating a disease, a carrier is required for introducing a useful substance such as a medicament and a physiologically active substance (hormone and lymphokine and the like) into a cell of a target tissue. Recently, with a progress of technology such as gene therapy and an antisense medical drug, development of a carrier has been aggressively made for efficiently introducing a specific gene and nucleic acid into a cell of a target tissue, particularly, in the field of cancer treatment and the like, the carrier has attracted attention as a novel therapy that may take the place of chemotherapy.

As a method for introducing a gene and a nucleic acid, (1) a viral vector method using a virus and (2) a method of using a non-viral vector such as a lipid membrane structure represented by a liposome are known.

In the former method, although the introduction efficiency thereof is high; however, the risk that viruses (adenovirus, herpes virus, vaccinia virus and RNA viruses such as retro virus) may cause cancer is pointed out as a problem. In addition, it is difficult to produce a large amount of viral vector. Antigenicity and toxicity to a host are also problems. These problems are causes of delaying practical application of gene therapy and the like, by the viral vector method.

In the latter method, Lipofectamine, Lipofectace, Lipofectin, Transfectam and Gene Transfer and the like are commercially available as cationized liposomes for Gene/nucleic acid introducing reagents. By use of these gene/nucleic acid introducing reagents, a gene and a nucleic acid can be introduced into culture cells. However, these gene/nucleic acid introducing reagents have drawbacks such as (a) poor stability of a lipid contained in a reagent, (b) unstable in the presence of the serum, (c) strong cytotoxicity and (d) need to further improve a gene/nucleic acid introduction efficiency into a cell. Because of the drawbacks, the gene/nucleic acid introducing reagents are not satisfactory as therapeutic drugs for gene therapy or nucleic acid medical drug treatment in humans or as reagents for introducing a gene/nucleic acid into animals by direct administration.

To introduce a gene/nucleic acid in vivo, it is desired to apply a gene/nucleic acid introducing reagent, which is a non-viral vector having less interaction with blood components, excellent stability, toxicity and pharmacokinetics and the like, as well as having more excellent introduction efficiency of a gene and a nucleic acid into a cell.

The problem to be solved by the present invention is to provide lipid membrane structures (a liposome, an emulsion and a micelle and the like) having further excellent gene/nucleic acid introduction efficiency and provide novel phospholipid derivatives useful as a main component of the lipid membrane structure.

SUMMARY OF THE INVENTION

The present inventors have conducted intensive studies in view of the aforementioned circumstances. As a result thereof, they were succeeded in synthesizing novel phospholipid derivatives and found that lipid membrane structures produced by the novel phospholipid derivatives (a liposome, an emulsion and a micelle and the like) are excellent in introduction efficiency of a gene and a nucleic acid into a cell. Based on the finding, the present invention was accomplished.

More specifically, the present invention provides novel phospholipid derivatives below and liposomes comprising the phospholipid derivatives.

[1] A compound represented by the general formula (1) below:

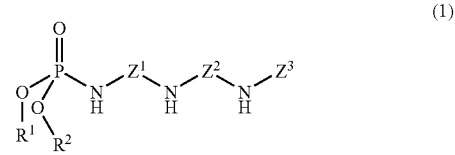

(1)

wherein
$R^1$ is an aliphatic hydrocarbon group having 10 to 22 carbon atoms;
$R^2$ is an aliphatic hydrocarbon group having 10 to 22 carbon atoms;
$Z^1$ is a C2-4 alkylene group;
$Z^2$ is a C2-3 alkylene group;
$Z^3$ is at least one selected from the group consisting of a hydrogen atom, $-Z^4-NH_2$, $-Z^4-NH-Z^5-NH_2$ and $-((CH_2)_2-NH)_q-H$;
$Z^4$ is a C2-4 alkylene group;
$Z^5$ is a C2-4 alkylene group; and
q is an integer of 3 to 5.

[2]
The compound according to the above item [1], in which $Z^1$ is $-CH_2-CH_2-$.

[3]
The compound according to the above item [1] or [2], in which $Z^2$ is $-CH_2-CH_2-$.

[4]
The compound according to any one of the above items [1] to [3], wherein $Z^3$ is $-((CH_2)_2-NH)_r-H$, wherein r is an integer of 0 to 4).

[5]
The compound according to any one of the above items [1] to [4], wherein $R^1$ is at least one selected from the group consisting of a dodecyl group, a tetradecyl group, a hexadecyl group, an octadecyl group and an octadecenyl group.

[6]
The compound according to any one of the above items [1] to [5], wherein $R^2$ is at least one selected from the group consisting of a dodecyl group, a tetradecyl group, a hexadecyl group, an octadecyl group and an octadecenyl group.

[7]
A compound represented by the general formula (2) below:

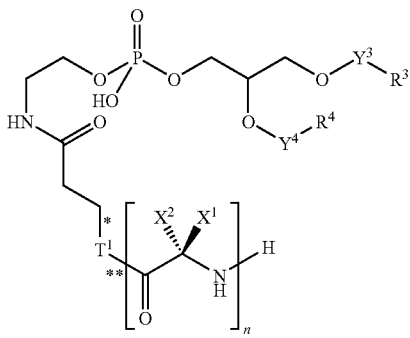

(2)

wherein
$R^3$ is an aliphatic hydrocarbon group having 10 to 22 carbon atoms;
$R^4$ is an aliphatic hydrocarbon group having 10 to 22 carbon atoms;
$Y^3$ is a methylene group or a carbonyl group;
$Y^4$ is a methylene group or a carbonyl group;
$X^1$ and $X^2$, which are different from each other, are a hydrogen atom or a group represented by —$(CH_2)_3$—NHC(=NH)NH$_2$;
$T^1$ is a group represented by the general formula (T2) or the general formula (T3) below:

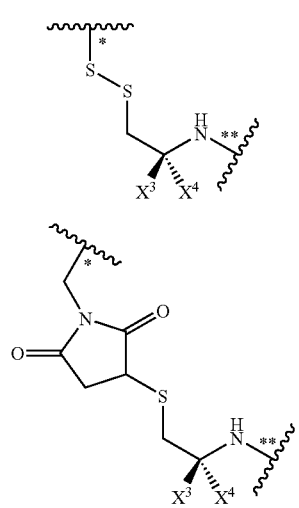

(T2)

(T3)

wherein
$X^3$ and $X^4$, which are different from each other, are a hydrogen atom or a carboxyl group; and
n is an integer selected from 4 to 12.
(In a compound represented by the general formula (2), the bond marked with * corresponds to the bond marked with * in the formula (T2) or (T3); the bond marked with  corresponds to the bond marked with  in the formula (T2) or (T3). The same is applied to the compound represented by the general formula (2-2) below.)

[8]
The compound according to the above item [7], wherein $R^3$ is at least one selected from the group consisting of an undecyl group, a tridecyl group, a pentadecyl group, a heptadecyl and a heptadecenyl group.

[9]
The compound according to the above item [7] or [8], wherein $R^4$ is at least one selected from the group consisting of an undecyl group, a tridecyl group, a pentadecyl group, a heptadecyl and a heptadecenyl group.

[10]
A compound represented by the general formula (I-2) below:

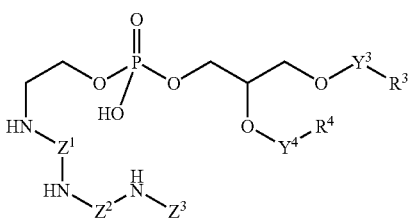

(1-2)

wherein
$R^3$ is an aliphatic hydrocarbon group having 10 to 22 carbon atoms;
$R^4$ represents an aliphatic hydrocarbon group having 10 to 22 carbon atoms;
$Y^3$ is a methylene group or a carbonyl group;
$Y^4$ is a methylene group or a carbonyl group;
$Z^1$ is a C2-4 alkylene group;
$Z^2$ is a C2-3 alkylene group;
$Z^3$ is at least one selected from the group consisting of a hydrogen atom, —$Z^4$—NH$_2$, —$Z^4$—NH—$Z^5$—NH$_2$ and —$((CH_2)_2$—NH$)_q$—H;
$Z^4$ is a C2-4 alkylene group;
$Z^5$ is a C2-4 alkylene group and
q is an integer of 3 to 5.

[11]
A compound represented by the general formula (2-2) below:

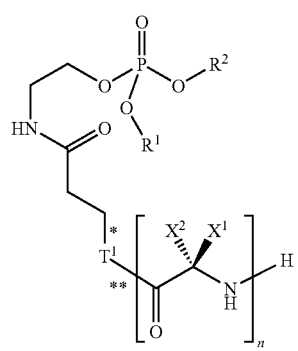

(2-2)

wherein
$R^1$ is an aliphatic hydrocarbon group having 10 to 22 carbon atoms;
$R^2$ is an aliphatic hydrocarbon group having 10 to 22 carbon atoms;
$T^1$ is a group represented by the general formula (T2) or the general formula (T3) below:

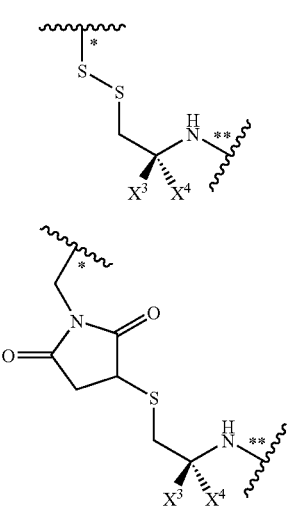

wherein

X¹ and X², which are different from each other, are a hydrogen atom or a group represented by —(CH$_2$)$_3$—NHC (=NH)NH$_2$;

X³ and X⁴, which are different from each other, are a hydrogen atom or a carboxyl group; and n is an integer selected from 4 to 12.

[13]
A lipid membrane structure comprising the compound according to any one of the above items [1] to [11] as a lipid component.

[14]
The lipid membrane structure according to above item [12], being a liposome.

[15]
The lipid membrane structure according to above item [12] or [13], holding an anti-tumor agent or a gene for a malignant tumor gene therapy.

[16]
The lipid membrane structure according to above item [7] or [8], in which the gene is a gene selected from the group consisting of an antisense oligonucleotide, antisense DNA, antisense RNA, shRNA and siRNA involved in vascularization or cell growth in a malignant tumor, and genes encoding physiologically active substances including enzymes and cytokines, antisense RNA, shRNA and siRNA.

[17]
A composition comprising the lipid membrane structure according to any one of the above items [12] to [16].

[18]
A method for introducing a gene, comprising a step of applying a composition comprising the lipid membrane structure according any one of the above items [12] to [16] to a cell in vivo (excluding a human) or in vitro.

[19]
A pharmaceutical composition for treating a malignant tumor, comprising the lipid membrane structure according any one of the above items [12] to [16].

[20]
A liposome comprising the compound according to any one of the above items [1] to [11] as a lipid component.

[21]
A liposome comprising the compound according to any one of the above items [1] to [11] in a membrane bilayer.

[22]
A liposome comprising the compound according to any one of the above items [1] to [11] as a component.

According to the present invention, it is possible to provide phospholipid derivatives useful for producing lipid membrane structures (a liposome, an emulsion and a micelle and the like) having excellent gene/nucleic acid introduction efficiency into a cell.

Furthermore, the lipid membrane structures (a liposome, an emulsion and a micelle and the like) of the present invention are useful as a therapeutic carrier and a laboratory reagent having excellent gene/nucleic acid introduction efficiency.

DETAILED DESCRIPTION OF THE INVENTION

Figure 1:
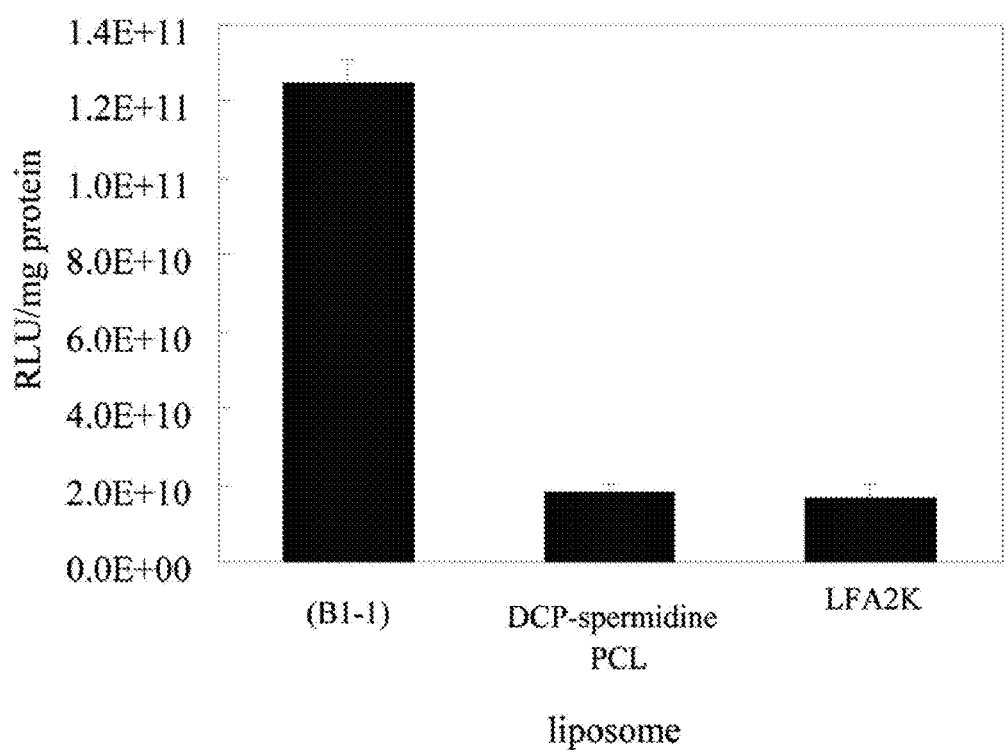
FIG. 1 shows gene results of transfection evaluation in Experimental Example B1.

The meaning of the terms and reference symbols and the like used in this specification will be described below and the best mode for carrying out the invention will be described more specifically. Note that the present invention is not limited to the best mode for carrying out the invention below and can be modified in various ways and carried out within the range of the gist thereof.

In a compound represented by the general formula (1), (1-2), (2-2) or (2) (hereinafter, sometimes referred to as a "phospholipid derivative (A)" or a "polycationized phospholipid derivative (A)"), the formula of the compound represents a predetermined isomer in this specification. However, the present invention includes all every possible isomers generated from the structure of the compound, such as geometrical isomers, optical isomers, stereoisomers, tautomers and mixtures of these isomers. The compound of the present invention is not limited to the description of the general formula. Any one of the isomers and a mixture thereof may be used. Furthermore, in the case of a tautomer, the compound may be an isomer mixture or in a transition state from an isomer to another isomer (an intermediate state between isomers) depending upon the compound.

Accordingly, the compound of the present invention may sometimes have an optical active substance and a racemate. Both are included in the present invention without any limitation. Furthermore, the compound of the present invention may have crystalline polymorphisms. They are not limited and the compound of the present invention may be any one of single crystalline forms and a mixture thereof. Moreover, anhydrous forms and hydrate forms may be included in the compound of the present invention.

In the specification of the present invention, the "aliphatic hydrocarbon group having 10 to 22 carbon atoms" refers to a straight or branched hydrocarbon group having 10 to 22 carbon atoms. Examples of the aliphatic hydrocarbon group having 10 to 22 carbon atoms include an alkyl group having 10 to 22 carbon atoms and an unsaturated hydrocarbon group having 10 to 22 carbon atoms, having double bond and/or triple bond in a total number of 1 to 3.

The "straight aliphatic hydrocarbon group having 10 to 22 carbon atoms" refers to a straight hydrocarbon group having 10 to 22 carbon atoms. Examples of the straight aliphatic hydrocarbon group having 10 to 22 carbon atoms include a straight alkyl group having 10 to 22 carbon atoms and an unsaturated hydrocarbon group having 10 to 22 carbon atoms, having double bond and/or triple bond in a total number of 1 to 3. Examples thereof include a decyl group ($-(CH_2)_9CH_3$), an undecyl group ($-(CH_2)_{10}CH_3$), a dodecyl group ($-(CH_2)_{11}CH_3$), a tridecyl group ($-(CH_2)_{12}CH_3$), a tetradecyl group ($-(CH_2)_{13}CH_3$), a pentadecyl group ($-(CH_2)_{14}CH_3$), a hexadecyl group ($-(CH_2)_{15}CH_3$), a heptadecyl group ($-(CH_2)_{16}CH_3$), an octadecyl group ($-(CH_2)_{17}CH_3$), a nonadecyl group ($-(CH_2)_{18}CH_3$), an icosyl group ($-(CH_2)_{19}CH_3$), a henicosyl group ($-(CH_2)_{20}CH_3$), a docosyl group ($-(CH_2)_{21}CH_3$) a hexadecenyl group, a heptadecenyl group, an octadecenyl group, an octadecadienyl group and an octadecatrienyl group.

The "straight saturated hydrocarbon group having 14 to 18 carbon atoms" refers to a straight alkyl group having 14 to 18 carbon atoms. Examples of the straight saturated hydrocarbon group having 14 to 18 carbon atoms include a group and the like represented by the formula: $-(CH_2)_m-CH_3$, wherein m represents an integer of 13 to 17, examples of which include a tetradecyl group ($-(CH_2)_{13}CH_3$), a pentadecyl group ($-(CH_2)_{14}CH_3$), a hexadecyl group ($-(CH_2)_{15}CH_3$), a heptadecyl group ($-(CH_2)_{16}CH_3$) and an octadecyl group ($-(CH_2)_{17}CH_3$).

The "straight unsaturated hydrocarbon group having 14 to 18 carbon atoms" refers to an unsaturated hydrocarbon group having 14 to 18 carbon atoms, having double bond and/or triple bond in a total number of 1 to 3. Examples of the straight unsaturated hydrocarbon group having 14 to 18 carbon atoms include a straight alkenyl group having 14 to 18 carbon atoms, a straight alkedienyl group having 14 to 18 carbon atoms, a straight alketrienyl group having 14 to 18 carbon atoms and a straight alkynyl group having 14 to 18 carbon atoms. Examples thereof may include a hexadecenyl group, an octadecenyl group, an octadecadienyl group and an octadecatrienyl group.

The "alkylene group having 2 to 4 carbon atoms" refers to a divalent group derived by removing an arbitrary single hydrogen atom from a "C2-4 alkyl group" (an ethyl group, a 1-propyl group (n-propyl group), a 2-propyl group (i-propyl group), a 2-methyl-1-propyl group (i-butyl group), a 2-methyl-2-propyl group (t-butyl group), a 1-butyl group (n-butyl group) and 2-butyl group (s-butyl group)). Examples of the C2-4 alkylene group include a 1,2-ethylene group, a 1,3-propylene group and a tetra methylene group ($-(CH_2)_4-$).

The "C2-3 alkylene group" refers to a divalent group derived by removing an arbitrary single hydrogen atom from an "C2-3 alkyl group" (an ethyl group, a 1-propyl group (n-propyl group) and a 2-propyl group (i-propyl group)). Examples of the C2-3 alkylene group include a 1,2-ethylene group and a 1,3-propylene group.

The "lipid membrane structure" refers to a particle having a membrane structure in which amphipathic lipid molecules are arranged with their polar groups positioned for the side of an aqueous phase of the interface. Examples of the lipid membrane structure include configurations such as a liposome, an emulsion, a micelle and an indeterminate-form laminate structure.

The "liposome" refers to a closed microsome, which is formed by forming a bilayer membrane of a phospholipid molecule with the hydrophobic moiety positioned inside and the hydrophilic moiety positioned outside, in water and closing the ends of the bilayer membrane. Examples of liposome include a microsome having a single layer formed of a phospholipid bilayer membrane and a microsome having a multiple layer formed of plural phospholipid bilayer. Since a liposome has such a structure, an aqueous solution is present at both inside and outside of the liposome and the liposome has structure in that the lipid bilayer serves as the boundary.

The "emulsion" refers to a liquid mixture in which liquid drops of a certain type of liquid (non-continuous phase) are dispersed in another type of immiscible liquid (a continuous phase). Example of form of the emulsion includes the form of oil in water emulsion (O/W type), water in oil emulsion (W/O type) or a complex emulsion (W/O/W type). A phospholipid component can be contained in either one of the liquid phases or in both liquid phases.

The "micelle" refers to an aggregate of amphipathic molecules. The micelle has a form in which a lipophilic moiety of this amphipathic molecules is positioned toward the center of the micelle and a hydrophilic moiety is positioned toward the outside thereof, in an aqueous medium. A center of a sphere is lipophilic and a peripheral portion is hydrophilic in such a micelle. Examples of a micelle structure include spherical, laminar, columnar, ellipsoidal, microsomal and lamellar structures, and a liquid crystal. Example of the micelle includes a polymer micelle having a water soluble polymer such as polyethylene glycol (PEG) as a hydrophilic domain, which has recently drawn attention as an amphipathic molecule.

Examples of the existence form of the lipid membrane structure include, but are not particularly limited to, dried form of a lipid mixture, dispersed form in an aqueous solvent, and a dried dispersed form or frozen dispersed form thereof.

When the existence form of the lipid membrane structure is dispersed form in an aqueous medium, the particle size of the lipid membrane structure is not particularly limited. In the case where the lipid membrane structure is a liposome or an emulsion, the particle size is, for example, 50 nm to several μm. In the case of a spherical micelle, the particle size is, for example, 5 nm to 50 nm.

In the case of a string-form micelle and indeterminate laminar structure, the thickness of a single layer is 5 nm to 10 nm and the single laminar structures may be stacked to form a multi layer.

In the lipid membrane structure of the present invention, as long as a phospholipid derivative (A) is contained in the membrane structure, other components contained in the membrane structure are not particularly limited.

A lipid membrane structure may be constituted only of a phospholipid derivative (A) and may contain other components such as other types of phospholipids and cholesterol.

As the other components in the lipid membrane structure, at least one type of molecule selected from the group consisting of phospholipids other than a phospholipid derivative (A); sterols such as cholesterol, cholesterol esters and cholestanol; glucuronic acid derivatives; and fatty acids having a saturated or unsaturated acyl group having 8 to 22 carbon atoms; polyethylene glycol derivatives (described in, e.g., Biochim. Biophys. Acta, 1029, 91 (1990); FEBS Lett. 268, 235 (1990)); and antioxidants such as α-tocopherol may be contained in the membrane structure.

Examples of "phospholipids other than a phospholipid derivative (A)" include phosphatidylethanolamine, phosphatidylcholine, phosphatidylserine, phosphatidylinositol, phosphatidylglycerol, cardiolipin, sphingomyelin, ceramide phosphorylethanolamine, ceramide phosphoryl glycerol, ceramide phosphoryl glycerol phosphate, 1,2-dimyristoyl-1, 2-deoxyphosphatidylcholine, plasmalogen, phosphatidic acid, L-dioleoylphosphatidylethanolamine (DOPE), egg-yolk lecithin and other phospholipids derived from natural products (e.g., soy-bean lecithin). These may be used alone or in a combination of two types or more.

Example of the fatty acid residues of the phospholipids other than a phospholipid derivative (A) includes, but are not particularly limited to, fatty acid residue having 12 to 18 carbon atoms. The fatty acid residues having 12 to 18 carbon atoms refer to straight or branched fatty acid residues having 12 to 18 carbon atoms. Examples of the fatty acid residues having 12 to 18 carbon atoms include an alkyl fatty acid residue having 12 to 18 carbon atoms, unsaturated hydrocarbon fatty acid residue having 12 to 18 carbon atoms having double bond and/or triple bond in a total number of 1 to 3. Examples thereof include a palmitoyl group, an oleoyl group, a stearoyl group and a linoleyl group.

As the phospholipids other than a phospholipid derivative (A), it is preferred to use phosphatidylethanolamine and phosphatidylcholine singly or in a combination of two types or more and more preferred to use phosphatidylethanolamine.

When a fatty acid membrane structure comprises a phospholipid derivative (A) and other components, the molar ratio of the phospholipid derivative (A) to other components is preferably 1:9 to 9:1, more preferably 2:8 to 8:2, and further preferably 3:7 to 7:3.

The cholesterol as other components is preferably 0 to 70%, more preferably 10 to 60%, and particularly preferably 20 to 50% in molar fraction.

Examples of the "aqueous solvent," in the "dispersion form in an aqueous solvent," include, but are not particularly limited, in addition to water, sugar solutions such as glucose, lactose and sucrose; aqueous polyhydric alcohol solutions such as glycerin and propylene glycol; physiological saline solution; buffer solutions such as a phosphate buffer solution, a citric acid buffer solution and a phosphate buffered saline solution; and mediums for cell culture.

[Meaning of $R^1$]

$R^1$ refers to an aliphatic hydrocarbon group having 10 to 22 carbon atoms.

Examples of $R^1$ include, preferably, a straight aliphatic hydrocarbon group having 10 to 22 carbon atoms; more preferably, a straight saturated hydrocarbon group having 14 to 18 carbon atoms and a straight unsaturated hydrocarbon group having 14 to 18 carbon atoms; further preferably, a dodecyl group, a tridecyl group, a tetradecyl group, a pentadecyl group, a hexadecyl group (a cetyl group), a heptadecyl group, an octadecyl group, a hexadecenyl group, an octadecenyl group, an octadecadienyl group and an octadecatrienyl group; further more preferably, a tetradecyl group, a hexadecyl group, an octadecyl group and an octadecenyl group (which refers to e.g., a straight alkenyl group having 18 carbon atoms (either cis or trans form, the position of a double bond is not limited)), such as an oleyl group, represented by the formula:

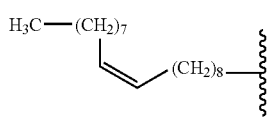

; and most preferably, a hexadecyl group.

[Meaning of $R^2$]

$R^2$ refers to an aliphatic hydrocarbon group having 10 to 22 carbon atoms.

Examples of $R^2$ include, preferably, a straight aliphatic hydrocarbon group having 10 to 22 carbon atoms; more preferably, a straight saturated hydrocarbon group having 14 to 18 carbon atoms and a straight unsaturated hydrocarbon group having 14 to 18 carbon atoms; further preferably, a dodecyl group, a tridecyl group, a tetradecyl group, a pentadecyl group, a hexadecyl group (a cetyl group), a heptadecyl group, an octadecyl group, a hexadecenyl group, an octadecenyl group, an octadecadienyl group and an octadecatrienyl group; and further more preferably, a tetradecyl group, a hexadecyl group, an octadecyl group and an octadecenyl group (which refers to e.g., a straight alkenyl group having 18 carbon atoms (either cis or trans form, the position of a double bond is not limited)), such as an oleyl group, represented by the formula:

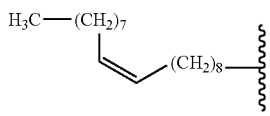

; and most preferably, a hexadecyl group.

[Meaning of $R^3$]

$R^3$ refers to an aliphatic hydrocarbon group having 10 to 22 carbon atoms.

Examples of $R^3$ include, preferably, a straight aliphatic hydrocarbon group having 10 to 22 carbon atoms; and more preferably, an undecyl group, a tridecyl group, a pentadecyl group, a heptadecyl group and a heptadecenyl group.

[Meaning of $R^4$]

$R^4$ refers to an aliphatic hydrocarbon group having 10 to 22 carbon atoms.

Examples of $R^4$ include, preferably, a straight aliphatic hydrocarbon group having 10 to 22 carbon atoms; and more preferably, an undecyl group, a tridecyl group, a pentadecyl group, a heptadecyl group and a heptadecenyl group.

[Meaning of $Z^1$]

$Z^1$ refers to a C2-4 alkylene group.

Examples of $Z^1$ include, preferably, $-CH_2-CH_2-$, $-CH_2-CH_2-CH_2-$ and $-CH_2-CH_2-CH_2-CH_2-$; more preferably, $-CH_2-CH_2-$ and $-CH_2-CH_2-CH_2-$; and further preferably, $-CH_2-CH_2-$.

[Meaning of $Z^2$]

$Z^2$ refers to a C2-3 alkylene group.

Examples of $Z^2$ include, preferably, $-CH_2-CH_2-$ and $-CH_2-CH_2-CH_2-$; and more preferably $-CH_2-CH_2-$.

[Meaning of $Z^3$]

$Z^3$ refers to at least one group selected from the group consisting of a hydrogen atom, $-Z^4-NH_2$, $-Z^4-NH-Z^5-NH_2$ and $-((CH_2)_2-NH)_q-H)$ ($Z^4$ represents a C2-4 alkylene group; $Z^5$ represents a C2-4 alkylene group; and q represents an integer of 3 to 5).

Examples of $Z^3$ include, preferably, a hydrogen atom and groups represented by $CH_2-CH_2-CH_2-NH_2$ and $-((CH_2)_2-NH)_r-H)$ (where r is an integer of 0 to 4).

[Meaning of $X^1$ and $X^2$]

$X^1$ and $X^2$, which are different from each other, refers to a hydrogen atom and $-(CH_2)_3-NHC(=NH)NH_2$.

Example of $X^1$ and $X^2$ includes preferably a case where $X^1$ is $-(CH_2)_3-NHC(=NH)NH_2$ and $X^2$ is a hydrogen atom.

[Meaning of $X^3$ and $X^4$]

$X^3$ and $X^4$, which are different from each other, refers to a hydrogen atom and a carboxyl group.

Example of $X^3$ and $X^4$ includes preferably a case where $X^3$ is a hydrogen atom and $X^4$ is a carboxyl group.

[Meaning of $Y^3$]

$Y^3$ refers to a methylene group or a carbonyl group.

Example of $Y^3$ includes preferably a carbonyl group.

[Meaning of $Y^4$]

$Y^4$ refers to a methylene group or a carbonyl group.

Example of $Y^4$ includes preferably a carbonyl group.

[Meaning of n]

Symbol n refers to an integer selected from 4 to 12.

Examples of n include, preferably, an integer selected from 4 to 9; more preferably 5 to 8; and further preferably 5 or 8.

The phospholipid derivative (A) of the present invention includes either of a free form, which does not form a salt, and a form of a salt with another molecule. When a compound itself is an amphoteric compound having both basic and acidic properties, the compound may form a salt between the molecules or within a molecule. Other than these forms, a mixture of these may be used. Furthermore, the phospholipid derivative (A) of the present invention may be present not only in a solid state but also in a dissolved state in a solution (including a solution containing various types of anion molecules and cation molecules as well as a solution controlled in pH) or in a suspended state. Alternatively, the compound may form a lipid membrane structure such as a liposome.

The "salt" is not particularly limited as long as it can form a salt with a phospholipid derivative (A) of the present invention and it is a pharmacologically acceptable. A salt with another molecule between the molecules may be formed and when the phospholipid derivative (A) itself is an amphoteric compound having both basic properties and acidic properties, an intramolecular salt may be formed. When a salt with another molecule is formed, examples of the another molecule forming the salt include an inorganic acid, an organic acid, an inorganic base, an organic base and an acidic or basic amino acid.

Examples of the salt include an inorganic acid salt, an organic acid salt, an inorganic base salt, an organic base salt and an acidic or basic amino acid salt.

Examples of the inorganic acid salt include hydrochloride, hydrobromide, sulfate, nitrate and phosphate.

Examples of the organic acid salt include acetate, succinate, fumarate, maleate, tartrate, citrate, lactate, stearate, benzoate, methanesulfonate, ethanesulfonate, p-toluenesulfonate and benzensulfonate.

Examples of the inorganic base salt include alkaline metals such as a sodium salt and a potassium salt; alkaline earth metal salts such as a calcium salt and a magnesium salt; aluminum salts and ammonium salts Examples of the organic base salt include a diethylamine salt, a diethanolamine salt, a meglumine salt and an N,N'-dibenzylethylenediamine salt.

Examples of the acidic amino salt include aspartate and glutamate.

Examples of the basic amino salt an arginine salt, a lysine salt and an ornithine salt.

The phospholipid derivative (A) of the present invention is a compound represented by the general formula (1), (2), (1-2) or (2-2) below:

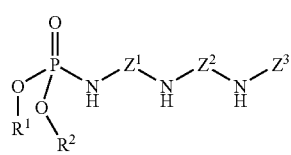

(1)

wherein $R^1$ is an aliphatic hydrocarbon group having 10 to 22 carbon atoms;

$R^2$ is an aliphatic hydrocarbon group having 10 to 22 carbon atoms;

$Z^1$ is a C2-4 alkylene group;

$Z^2$ is a C2-3 alkylene group;

$Z^3$ is at least one selected from the group consisting of a hydrogen atom, $-Z^4-NH_2$, $-Z^4-NH-Z^5-NH_2$ and $-((CH_2)_2-NH)_q-H$;

$Z^4$ is a C2-4 alkylene group;

$Z^5$ is a C2-4 alkylene group; and q is an integer of 3 to 5.

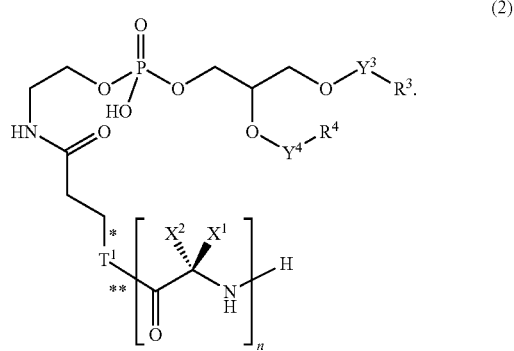

(2)

wherein $R^3$ is an aliphatic hydrocarbon group having 10 to 22 carbon atoms;

$R^4$ is an aliphatic hydrocarbon group having 10 to 22 carbon atoms;

$Y^3$ is a methylene group or a carbonyl group;

$Y^4$ is a methylene group or a carbonyl group;

$X^1$ and $X^2$, which are different from each other, are a hydrogen atom or a group represented by $-(CH_2)_3-NHC(=NH)NH_2$;

$T^1$ is a group represented by the general formula (T2) or the general formula (T3).

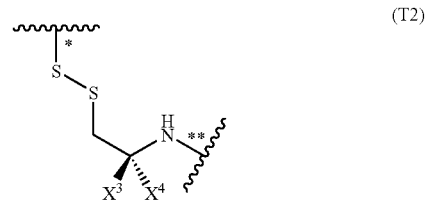

(T2)

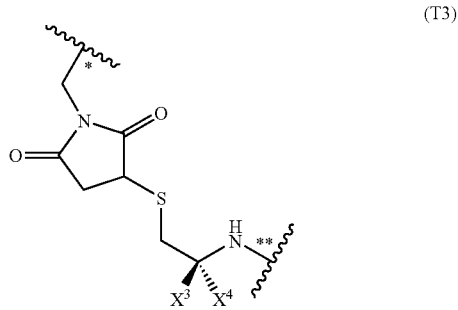

(T3)

wherein $X^3$ and $X^4$, which are different from each other, are a hydrogen atom or a carboxyl group; and n is an integer selected from 4 to 12.

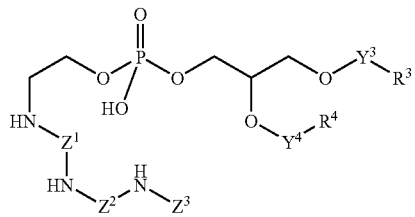
(1-2)

wherein

R³ is an aliphatic hydrocarbon group having 10 to 22 carbon atoms;

R⁴ is an aliphatic hydrocarbon group having 10 to 22 carbon atoms;

Y³ is a methylene group or a carbonyl group;

Y⁴ is a methylene group or a carbonyl group;

$Z^1$ is a C2-4 alkylene group;

$Z^2$ is a C2-3 alkylene group;

$Z^3$ is at least one selected from the group consisting of a hydrogen atom, $-Z^4-NH_2$, $-Z^4-NH-Z^5-NH_2$ and $-((CH_2)_2-NH)_q-H$;

$Z^4$ is a C2-4 alkylene group;

$Z^5$ is a C2-3 alkylene group; and q is an integer of 3 to 5.

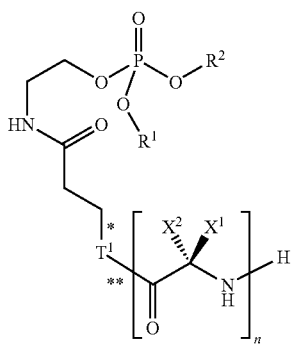
(2-2)

wherein

R¹ is an aliphatic hydrocarbon group having 10 to 22 carbon atoms;

R² is an aliphatic hydrocarbon group having 10 to 22 carbon atoms;

T¹ is a group represented by the general formula (T2) or the general formula (T3) below:

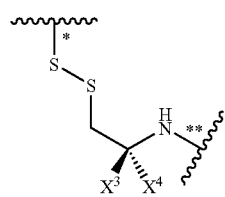
(T2)

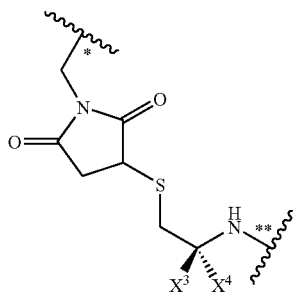
(T3)

wherein

X¹ and X², which are different from each other, are a hydrogen atom or a group represented by $-(CH_2)_3-NHC(=NH)NH_2$;

X³ and X⁴, which are different from each other, are a hydrogen atom or a carboxyl group; and n is an integer selected from 4 to 12.

A compound of the present invention represented by the general formula (1), (1-2), (2-2) or (2) (phospholipid derivative (A)) can be produced by the methods described below; however, the method for producing the compound of the present invention is not limited to these.

Production method A

Production method A is a method for producing a compound represented by the general formula (1) and production method A is as described in the following scheme.

[Formula 15]

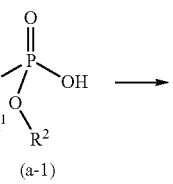
(a-1)

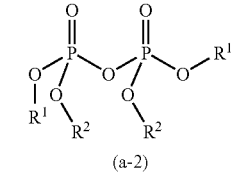 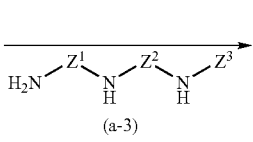
(a-2)

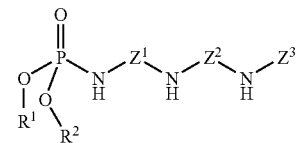
(1)

(In each formula of the above scheme, R¹, R², $Z^1$, $Z^2$ and $Z^3$ are the same as defined in the general formula (1) above.)

[Step A1]

Step A1 is a step for producing a compound (a-2) by reacting a compound (a-1) in the presence of a base and a condensation agent in a solvent.

Step A1 can be carried out in accordance with a generally employed method as described in, e.g., Chemistry and Industry (London, United Kingdom) 367-377 (1960) and Japanese Patent Laid-Open No. 2005-247751. Further specifically, Step A1, can be carried out with reference to the reaction conditions, post-reaction operations and purification methods described in Production Examples 2, 4 and 6 (later described).

Step A1 can be also carried out under air flow or an atmosphere of an inert gas such as nitrogen and argon.

As the compound (a-1), a known compound, a commercially available compound, a compound readily produced from a commercially available compound by a customary method for those skilled in the art, a compound that can be synthesized by the method described in Japanese Patent Laid-Open No. 2005-247751 and the like, and a compound that can be produced by production method B below or Production Example 1, 3 or 5 can be used.

The solvent to be used in Step A1 is not particularly limited as long as it can dissolve the starting material to some extent and does not inhibit a reaction. For example, halogenated hydrocarbon solvents such as chloroform and dichloroethane; ether solvents such as tetrahydrofuran, 1,2-dimethoxyethane, methyl-t-butyl ether, cyclopentyl methyl ether, diethyl ether, diisopropyl ether, dibutyl ether and dicyclo pentyl ether; aromatic hydrocarbon solvents such as benzene and toluene; basic organic compounds which are present in a liquid state under normal-temperature/normal-pressure conditions, such as pyridine, triethylamine, tripropylamine, 1-methylimidazole and 1,2-dimethylimidazole, or a solvent mixture of these can be used, and examples thereof include, preferably, a basic organic compounds which are present in a liquid state under normal-temperature/normal-pressure conditions such as pyridine, triethylamine, tripropylamine, 1-methylimidazole and 1,2-dimethylimidazole, and more preferably, pyridine (anhydrous pyridine) having a moisture content of 50 ppm or less.

Examples of the base in Step A1 include pyridine, triethylamine, tripropylamine, 1-methylimidazole and 1,2-dimethylimidazole; preferably, pyridine; and more preferably, pyridine (anhydrous pyridine) having a moisture content of 50 ppm or less. The base can be used in an amount of 2 to 10 times moles based on the compound (a-1).

Examples of the condensation agent to be used in Step A1, 1,3,5-triisopropylbenzene sulfonyl chloride, 2,4,6-triisopropylbenzene sulfonyl chloride, 2,4,6-trimethylbenzene sulfonyl chloride and nitrosyl chloride; and preferably, 1,3,5-triisopropylbenzene sulfonyl chloride. The condensation agent can be used in an amount of 3 to 15 times moles based on the compound (a-1).

In Step A1, the reaction temperature usually varies depending upon the starting material, solvent and others such as the reagent to be used in the reaction; however, it is preferably 10° C. to 30° C. (interior temperature of a reaction container).

The reaction time usually varies depending upon the starting material, solvent, others such as the reagent to be used in the reaction and the reaction temperature. However, preferably, after a reagent is added, a reaction is preferably carried out for 30 minutes to 3 hours at the aforementioned temperature while stirring.

[Step A2]

Step A2 is a step for producing a compound represented by the general formula (1) of the present invention by reacting a compound (a-2) and a compound (a-3) in a solvent.

More specifically, Step A2 can be carried out with reference to the reaction conditions, post-reaction operations and purification method described in Example 1 (later described). This reaction can be also carried out under air flow or an atmosphere of an inert gas such as nitrogen and argon.

As the compound (a-3), a known compound represented by the formula,

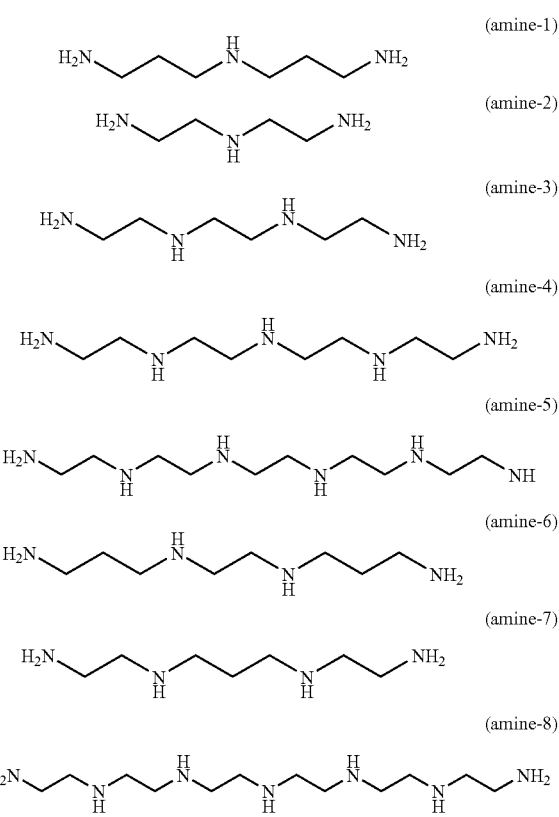

a commercially available compound, a compound readily produced from a commercially available compound by a customary method for those skilled in the art and the like can be used.

The compound (a-3) can be used in an amount of 1 to 6 times moles based on the compound (a-2).

The solvent to be used in Step A2 is not particularly limited as long as it can dissolve the starting materials to some extent and does not inhibit a reaction. Examples thereof include pyridine, triethylamine, tripropylamine, 1-methylimidazole and 1,2-dimethylimidazole; preferably, pyridine; and more preferably, pyridine (anhydrous pyridine) having a moisture content of 50 ppm or less.

In Step A2, the reaction temperature usually varies depending upon the starting material, solvent and others such as the reagent to be used in the reaction; however, it is preferably 0° C. to 40° C. (interior temperature of a reaction container), and more preferably 20° C. to 30° C. (interior temperature of a reaction container).

The reaction time usually varies depending upon the starting material, solvent, others such as the reagent to be used in the reaction and the reaction temperature. However, preferably, after a reagent is added, a reaction is preferably carried out for 1 hour to 2 days, and more preferably for about 6 hours at the aforementioned temperature while stirring.

Production Method B

Production method B is a method for producing a compound (a-1) and production method B is as described in the following scheme.

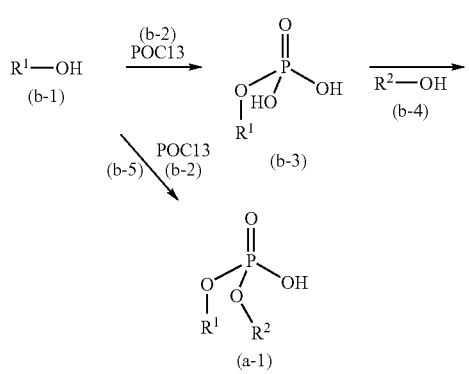

(In each formula of the above scheme, $R^1$ and $R^2$ are the same as defined in the general formula (1) above.)

[Step B1]

Step B1 is a step for producing a compound (b-3) by reacting a compound (b-1) and a compound (b-2) (phosphorus oxychloride) in the presence of a base in a solvent.

Step B1 can be carried out in accordance with a generally employed method as described in, Biochemistry, 13, 2754 (1974); and Biochim. Biophys. Acta, 553, 476 (1979); Jikken Kagaku Kouza 22, (4th edition), Organic Synthesis IV, Maruzen (1992), p. 313-368 and the like.

Step B1 can be also carried out under air flow or an atmosphere of an inert gas such as nitrogen and argon.

As the compound (b-1), a known compound, such as lauryl alcohol, myristyl alcohol, cetyl alcohol, 1-octadecanol, 1-eicosanol or oleyl alcohol, a commercially available compound or a compound readily produced from a commercially available compound by a customary method for those skilled in the art can be used.

The solvent to be used in Step B1 is not particularly limited as long as it can dissolve the starting materials to some extent and does not inhibit a reaction. For example, tetrahydrofuran, dioxane, acetonitrile, pyridine, nitromethane, dichloromethane, acetone, chloroform, dimethylformamide, trimethylphosphate (($MeO)_3P=O$)), triethyl phosphoric acid (($EtO)_3P=O$)) or a solvent mixture containing these solvents and water, methanol, ethanol or t-butanol, or the like can be used.

Examples of the base in Step B1 include triethylamine and pyridine.

In Step B1, the reaction temperature usually varies depending upon the starting material, solvent and others such as the reagent to be used in the reaction; however, it is preferably $-10°$ C. to $40°$ C. (interior temperature of a reaction container).

The reaction time usually varies depending upon the starting material, solvent, others such as the reagent to be used in the reaction and reaction temperature. However, preferably, after a reagent is added, a reaction is preferably performed for 10 minutes to 6 hours, and more preferably for about 30 minutes at the aforementioned temperature, while stirring.

As described above, after a compound (b-1) and a compound (b-2) (phosphorus oxychloride) are reacted, an ice-cooled or cooled aqueous basic solution (an aqueous sodium hydrogen carbonate solution or an aqueous ethylenediamine tetraacetic acid solution) is added dropwise to the reaction solution, or the reaction solution is added dropwise to an ice-cooled or cooled aqueous basic solution (an aqueous sodium hydrogen carbonate solution or an aqueous ethylenediamine tetraacetic acid solution) and appropriately stirred. Furthermore, to the reaction solution, if necessary, an appropriate pH controlling solution is added.

[Step B2]

Step B2 is a step for producing a compound (a-1) by reacting a compound (b-3) and a compound (b-4) in the presence of a condensation agent (b-5) in a solvent.

This step can be carried out by the method generally employed and described in Biochemistry, 8, 3067 (1969); Chem. Ber., 94, 996 (1961); Chem. Ber., 98, 3286 (1965); J. Chem. Soc., Chem. Commun., 1974, 997; Tetrahedron Lett., 14, 1353 (1973); Justus Liebigs Ann. Chem., 692, 22 (1966); Angew. Chem., 73, 220 (1961); and Jikken Kagaku Kouza 22 (4th edition), Organic Synthesis IV, Maruzen (1992), p. 368-446.

Step B2 can be also carried out under air flow or an atmosphere of an inert gas such as nitrogen and argon.

The compounds that can be used as the compound (b-4) are the same as described in the compound (b-1) above.

The solvent to be used in Step B2 is not particularly limited as long as it can dissolve the starting materials to some extent and does not inhibit a reaction and appropriately selected depending upon the condensation agent (b-5). For examples, pyridine and a solvent mixture of pyridine and dimethylformamide can be used.

Examples of the condensation agent (b-5) in Step B2 include 1,3,5-triisopropylbenzene sulfonyl chloride, 2,4,6-triisopropylbenzene sulfonyl chloride, 2,4,6-trimethylbenzene sulfonyl chloride, dicyclohexylcarbodiimide, trichloroacetonitrile, p-tolyl cyanate, cyclohexyl isocyanide, p-toluenesulfonic acid imidazolide, mesitylenesulfonic acid imidazolide, 2,4,6-triisopropyl benzenesulfonic acid imidazolide, a phosphonium salt produced from α-bromo-α-cyanoacetamide and a triphenylphosphine, and cyanuric chloride.

In Step B2, the reaction temperature usually varies depending upon the starting material, solvent and others such as the reagent to be used in the reaction; however, it is preferably $0°$ C. to $100°$ C. (interior temperature of a reaction container).

The reaction time usually varies depending upon the starting material, solvent, others such as the reagent to be used in the reaction and the reaction temperature. However, preferably, after a reagent is added, a reaction is preferably carried out for 30 minutes to 24 hours at the aforementioned temperature while stirring.

[Step B3]

Step B3 is a step for producing a compound (a-1) (a compound wherein $R^1$ and $R^2$ are the same group) by reacting a compound (b-1) and a compound (b-2) (phosphorus oxychloride) in a solvent.

The reaction conditions of Step B3 can be set with reference to the reaction conditions described in Step B1 of production method B. More specifically, to this step, the same reaction conditions, post reaction operation, and the conditions and operation of the purification method as those in Production Examples 1, 3 and 5 (described later) can be applied.

Production Method X

Production method X is a method for producing a compound represented by the general formula (2) and production method X is as described in the following scheme.

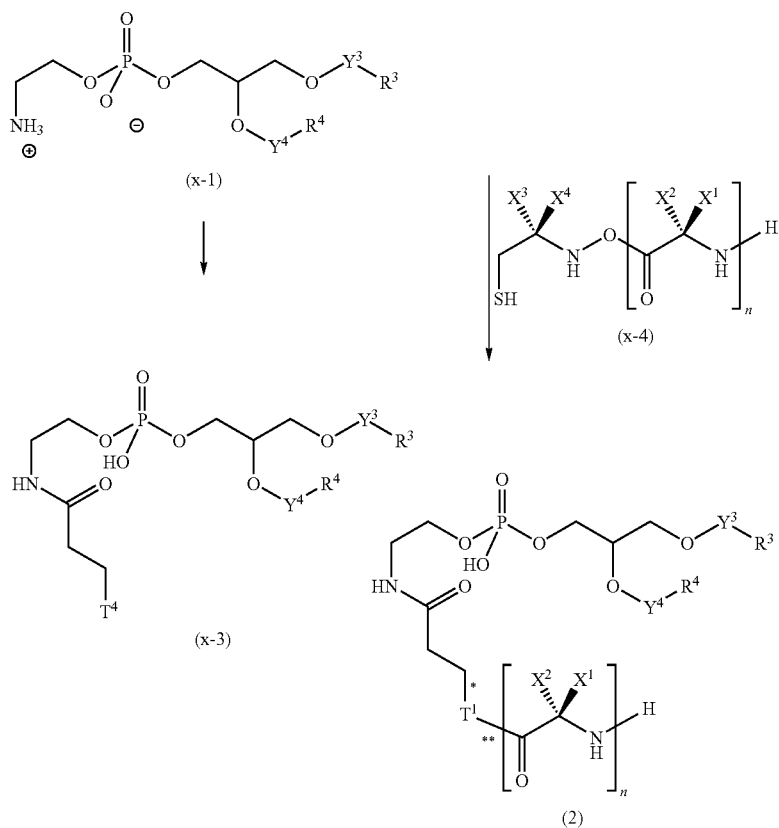

(In each formula of the above scheme, $R^3$, $R^4$, $Y^3$, $Y^4$, $T^1$, $X^1$, $X^2$, $X^3$, $X^4$ and n are the same as defined in the general formula (2) above; $T^4$ is a group represented by the formula (T5) and (T6) below.)

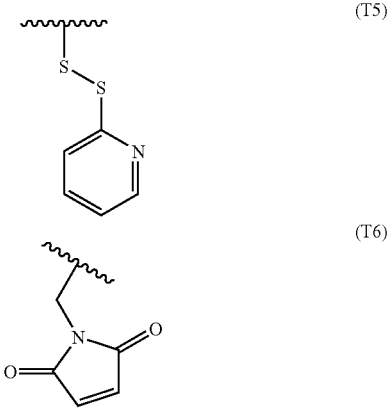

[Step X1]

Step X1 is a step for producing a compound (x-3) by reacting a compound (x-1) and a compound (x-2) (N-succinimidyl-3-(2-pyridyldithio)propionate (SPDP) or N-(4-maleimidebutyloxy)succinimide) in the presence of a base in a solvent.

More specifically, Step X1 can be carried out with reference to the reaction conditions, post-reaction operations and purification methods described in Production Examples 7 and 8 (later described).

Step X1 can be also carried out under air flow or an atmosphere of an inert gas such as nitrogen and argon.

As the compound (x-1), a known compound described in Japanese Patent Laid-Open No. 2005-247751 and the like, a commercially available compound, a compound readily produced from a commercially available compound by a customary method for those skilled in the art, a compound that can be produced by production method Y below can be used.

The solvent to be used in Step X1 is not particularly limited as long as it can dissolve a starting material to some extent and does not inhibit a reaction. For example, halogenated hydrocarbon solvents such as chloroform and methylene chloride and the like can be used.

As the base in Step X1, for example, triethylamine and diisopropylethylamine can be used.

In Step X1, the reaction temperature usually varies depending upon the starting material, solvent and others such as the reagent to be used in the reaction; however, it is preferably 20° C. to 50° C. (interior temperature of a reaction container).

The reaction time usually varies depending upon the starting material, solvent, others such as the reagent to be used in the reaction and reaction temperature. However, generally, after a reagent is added, a reaction is carried out for 1 to 40 hours at the aforementioned temperature while stirring.

[Step X2]

Step X2 is a step for producing a compound represented by the general formula (2) by reacting a compound (x-3) and a compound (x-4).

More specifically, Step X2 can be carried out with reference to the reaction conditions, post-reaction operations and purification methods described in Production Examples 5 and 6 (later described).

Step X2 can be also carried out under air flow or an atmosphere of an inert gas such as nitrogen and argon.

As the compound (x-4), a commercially available peptide such as Arg-Arg-Arg-Arg-Arg-Cys (the left side represents the N terminal) or a compound readily produced from a commercially available compound by a customary method for those skilled in the art can be used.

The solvent to be used in Step X2 is not particularly limited as long as it can dissolve the starting materials to some extent and does not inhibit a reaction. For example, alcohol solvents such as methanol, ethanol and propanol; halogenated hydrocarbon solvents such as chloroform and methylene chloride; water; a solvent mixture of these; and the like; preferably, a mixture containing chloroform, methanol and water, a solvent mixture containing chloroform, methanol and water in a ratio of about 13/6/1 (by volume) can be used.

In Step X2, the reaction temperature usually varies depending upon the starting material, solvent and others such as the reagent to be used in the reaction; however, it is preferably 0° C. to 40° C. (interior temperature of a reaction container).

The reaction time usually varies depending upon the starting material, solvent, others such as the reagent to be used in the reaction and reaction temperature. Preferably, after a reagent is added, a reaction is generally carried out for 1 to 24 hours at the aforementioned temperature while stirring.

Production Method Y

Production method Y is a method for producing a compound (x-1) as a raw material in Production method X and production method Y is as described in the scheme below:

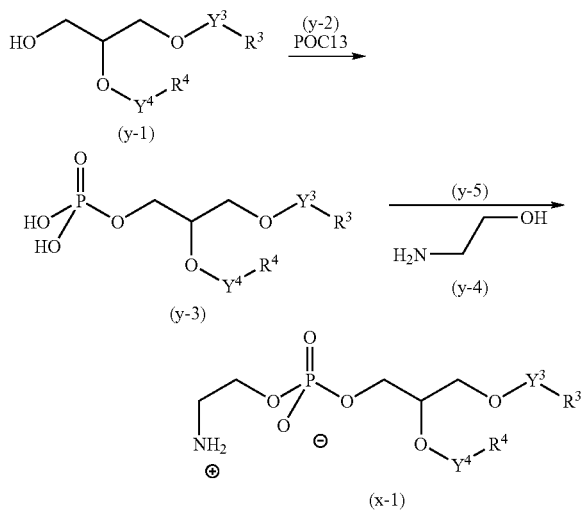

(In each formula of the above scheme, $R^3$, $R^4$, $Y^3$ and $Y^4$ are the same as defined in the general formula (2).)

[Step Y1]

Step Y1 is a step for producing a compound (y-3) by reacting a compound (y-1) and a compound (y-2) (phosphorus oxychloride) in a solvent.

As the compound (y-1), a known compound, a commercially available compound and a compound readily produced from a commercially available compound by a customary method for those skilled in the art can be used.

The reaction conditions of Step Y1 are the same as the conditions and operation method as in Step B1 of production method B.

[Step Y2]

Step Y2 is a step for producing a compound (x-1) by reaction a compound (y-3) and a compound (y-4) in the presence of a condensation agent (y-5) in a solvent.

As the reaction conditions of Step Y2, the same conditions and operation method as in Step B2 of production method B can be applied.

A compound represented by the general formula (I-2) or a compound represented by the general formula (2-2) can be produced by carrying out the reaction steps, reaction conditions and raw materials of the production method above in appropriate combination. Furthermore, reaction conditions may be appropriately changed.

Representative examples of a method for producing a phospholipid compound (A) according to the present invention have been described above. The raw material compounds and reagents may form a salt, a hydrate or a solvate; each may vary depending upon the starting material and the solvent to be used; and is not particularly limited as long as they do not inhibit the reaction. The solvent to be used varies depending upon a starting material and reagents and the like. Needless to say, the solvent is not particularly limited as long as it can dissolve starting material(s) to some extent and does not inhibit a reaction. When a compound according to the present invention is obtained in the form of a free form, it can be converted into a salt or a hydrate which the compound may be formed into, in accordance with the customary method.

In particular, when substances except a desired compound contained in a reaction mixture do not inhibit the reaction of the next step, the reaction mixture can be also directly used in the next step without particularly isolating the desired compound.

In each of the aforementioned methods, after the reaction of the steps is completed, a desired compound of each step can be collected from a reaction mixture in accordance with the customary method.

For example, when a whole reaction mixture is liquid, if desired, the reaction mixture is returned to room temperature or ice cooled. Appropriately, acid, alkali, an oxidizing agent or a reducing agent is neutralized. Water and an organic solvent such as ethyl acetate immiscible and non-reactive with a desired compound are added to separate a layer containing the desired compound. Next, a solvent that is immiscible with the obtained layer and non-reactive with the desired compound is added to wash the layer containing the desired compound and the layer is separated. In addition, if the layer is an organic layer, it is dried by use of a drying agent such as anhydrous magnesium sulfate or anhydrous sodium sulfate to evaporate the solvent. In this manner, the desired compound can be obtained. Furthermore, if the layer is an aqueous layer, the layer is electrically desalted and thereafter lyophilized. In this manner, the desired compound can be obtained.

To improve the purity of the desired compound obtained by the aforementioned method, appropriately, recrystallization, various chromatographic methods (including normal-phase column chromatography, reversed-phase column chromatography and thin-layer chromatography) and an evaporation method can be carried out.

Based on the conditions and operation methods described in the aforementioned production methods and Examples below, the compounds listed in Table 1 below can be synthesized by using lauryl alcohol, myristyl alcohol, cetyl alcohol, 1-octadecanol, 1-eicosanol and oleyl alcohol as the raw materials (the compound (b-1), the compound (b-4), the compound (c-1) and the compound (c-4) and the like in the above production methods) for introducing $R^1$ and $R^2$ and by using amine-1 to amine-8 represented by the formulas below as the raw material (the compound (a-3) and the like of the above production methods) and the like for introducing a polyamine site.

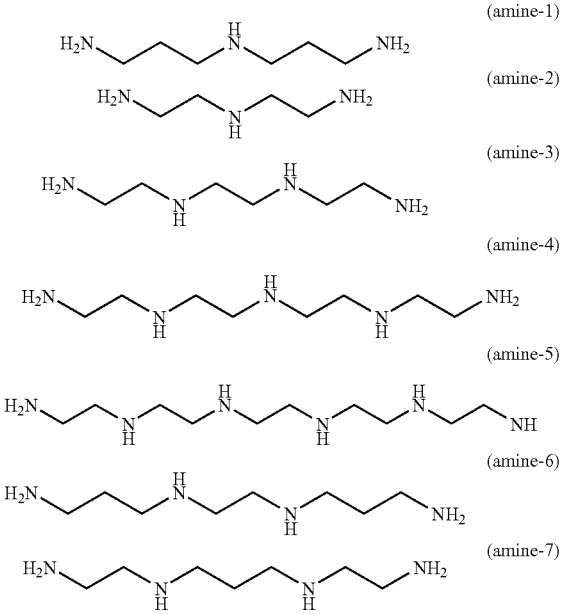

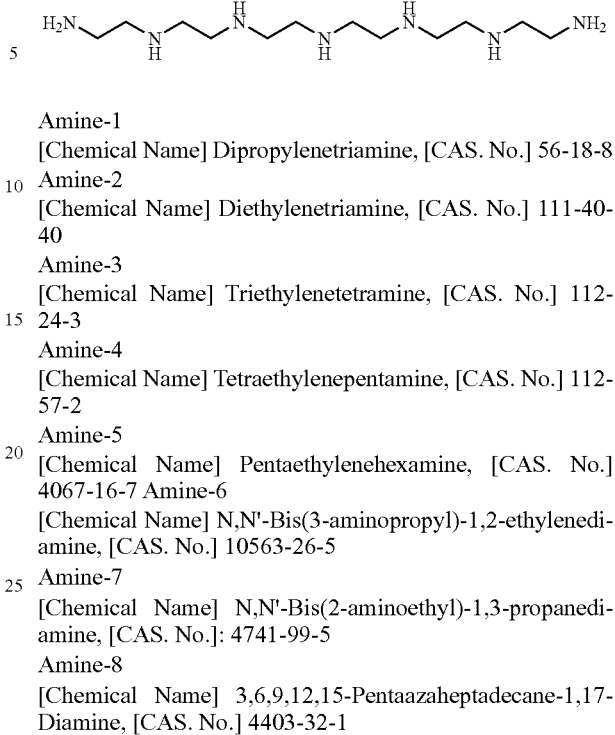

Amine-1
[Chemical Name] Dipropylenetriamine, [CAS. No.] 56-18-8
Amine-2
[Chemical Name] Diethylenetriamine, [CAS. No.] 111-40-40
Amine-3
[Chemical Name] Triethylenetetramine, [CAS. No.] 112-24-3
Amine-4
[Chemical Name] Tetraethylenepentamine, [CAS. No.] 112-57-2
Amine-5
[Chemical Name] Pentaethylenehexamine, [CAS. No.] 4067-16-7
Amine-6
[Chemical Name] N,N'-Bis(3-aminopropyl)-1,2-ethylenediamine, [CAS. No.] 10563-26-5
Amine-7
[Chemical Name] N,N'-Bis(2-aminoethyl)-1,3-propanediamine, [CAS. No.]: 4741-99-5
Amine-8
[Chemical Name] 3,6,9,12,15-Pentaazaheptadecane-1,17-Diamine, [CAS. No.] 4403-32-1

TABLE 1

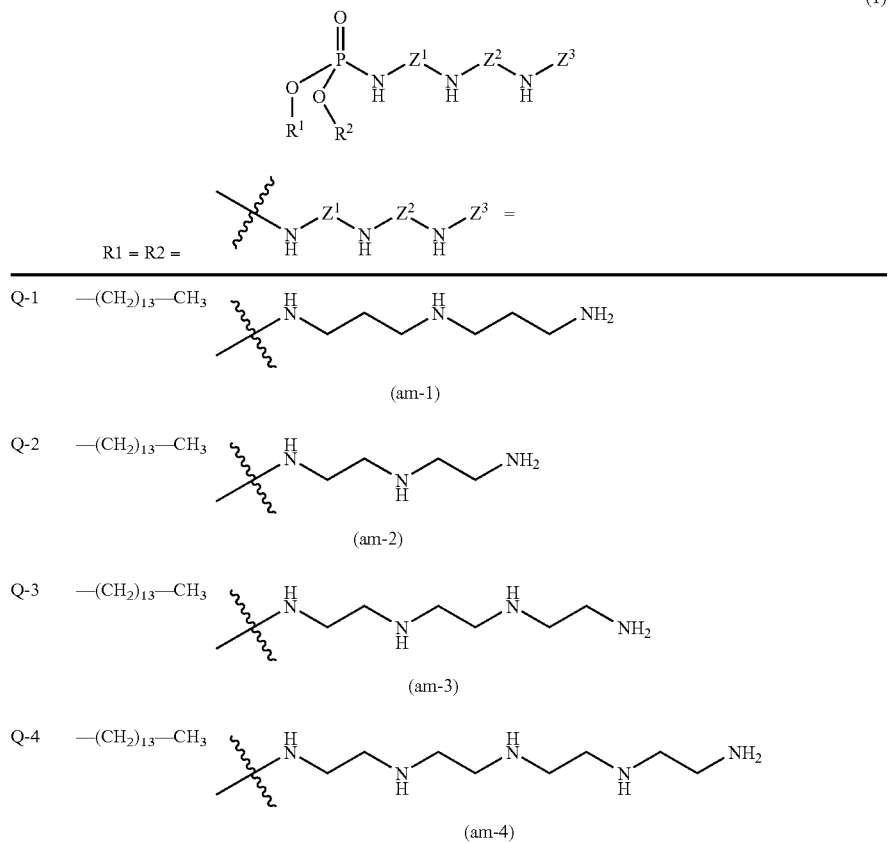

TABLE 1-continued $$\text{(1)} \quad \underset{R^1}{\overset{O}{\underset{O}{\parallel}}}\underset{R^2}{\overset{O}{\underset{H}{P}}}\underset{H}{\overset{Z^1}{\underset{H}{N}}}\underset{H}{\overset{Z^2}{\underset{H}{N}}}Z^3$$

| | R1 = R2 = | $\sim\!\!\!\!\underset{H}{N}\!\!-\!\!Z^1\!\!-\!\!\underset{H}{N}\!\!-\!\!Z^2\!\!-\!\!\underset{H}{N}\!\!-\!\!Z^3$ = |
|---|---|---|
| Q-5 | —(CH$_2$)$_{13}$—CH$_3$ | (am-5) |
| Q-6 | —(CH$_2$)$_{13}$—CH$_3$ | (am-6) |
| Q-7 | —(CH$_2$)$_{13}$—CH$_3$ | (am-7) |
| Q-8 | —(CH$_2$)$_{13}$—CH$_3$ | (am-8) |
| Q-9 | —(CH$_2$)$_{15}$—CH$_3$ | (am-1) |
| Q-10 | —(CH$_2$)$_{15}$—CH$_3$ | (am-2) |
| Q-11 | —(CH$_2$)$_{15}$—CH$_3$ | (am-3) |
| Q-12 | —(CH$_2$)$_{15}$—CH$_3$ | (am-4) |
| Q-13 | —(CH$_2$)$_{15}$—CH$_3$ | (am-5) |
| Q-14 | —(CH$_2$)$_{15}$—CH$_3$ | (am-6) |
| Q-15 | —(CH$_2$)$_{15}$—CH$_3$ | (am-7) |
| Q-16 | —(CH$_2$)$_{15}$—CH$_3$ | (am-8) |
| Q-17 | —(CH$_2$)$_{17}$—CH$_3$ | (am-1) |
| Q-18 | —(CH$_2$)$_{17}$—CH$_3$ | (am-2) |
| Q-19 | —(CH$_2$)$_{17}$—CH$_3$ | (am-3) |
| Q-20 | —(CH$_2$)$_{17}$—CH$_3$ | (am-4) |
| Q-21 | —(CH$_2$)$_{17}$—CH$_3$ | (am-5) |
| Q-22 | —(CH$_2$)$_{17}$—CH$_3$ | (am-6) |
| Q-23 | —(CH$_2$)$_{17}$—CH$_3$ | (am-7) |
| Q-24 | —(CH$_2$)$_{17}$—CH$_3$ | (am-8) |
| Q-25 | —(CH$_2$)$_{19}$—CH$_3$ | (am-1) |
| Q-26 | —(CH$_2$)$_{19}$—CH$_3$ | (am-2) |
| Q-27 | —(CH$_2$)$_{19}$—CH$_3$ | (am-3) |
| Q-28 | —(CH$_2$)$_{19}$—CH$_3$ | (am-4) |
| Q-29 | —(CH$_2$)$_{19}$—CH$_3$ | (am-5) |
| Q-30 | —(CH$_2$)$_{19}$—CH$_3$ | (am-6) |
| Q-31 | —(CH$_2$)$_{19}$—CH$_3$ | (am-7) |
| Q-32 | —(CH$_2$)$_{19}$—CH$_3$ | (am-8) |
| Q-33 | | (am-1) |
| Q-34 | | (am-2) |
| Q-35 | | (am-3) |
| Q-36 | | (am-4) |
| Q-37 | | (am-5) |
| Q-38 | | (am-6) |
| Q-39 | | (am-7) |
| Q-40 | | (am-8) |

[Preparation Method for a Lipid Membrane Structure]

A method for producing a lipid membrane structure comprising a phospholipid derivative (A) is not particularly limited; however, the lipid membrane structure can be produced, for example, as follows.

I) Method for Producing a Liposome Comprising a Phospholipid Derivative (A)

A liposome water-dispersion solution is prepared using substances as a membrane component including a phospholipid derivative (A), phospholipid except the phospholipid derivative (A), such as phosphatidylcholine, sphingomyelin and phosphatidylethanolamine, a glycolipid, and a dialkyl based synthetic surfactant in accordance with a known method [Annual review of biophysics and bioengineering, 9,467 to 508 (1980)]. The liposome may contain sterols such as cholesterol and cholestanol as a membrane stabilizer; charged substances such as a dialkyl phosphate, diacyl phosphatidic acid and stearyl amine; and an antioxidant such as α-tocopherol. To the prepared liposome water-dispersion solution, an aqueous solution of the phospholipid derivative (A) is added and allowed to stand still for a predetermined time, or preferably to be heated to not less than a phase transition temperature of the membrane or 40° C. or more and then gradually cooled. In this manner, a desired liposome comprising a phospholipid derivative (A) can be produced.

A desired liposome can be also produced also by mixing the substances serves as membrane components and a phospholipid derivative A in advance and treated in accordance with a known liposome production method.

The liposome of the present invention can be prepared by general methods and conditions described below:
(1) "liposome" edited by Shosichi Nojima et al., Nankodo (1988), p. 26;
(2) "Biomembrane experimental method (second half)" Kyoritsu (1974), p. 185;
(3) "The 4th edition, Jikken Kagaku Kouza 27 bioorganic", Maruzen (1991) p. 92-104;
(4) "The 4th edition, Jikken Kagaku Kouza 13, surface/interface", Maruzen (1993), p. 92-104;
(5) F. Szoka and D. Papahadjopoulos, "Liposomes: from physical structure to therapeutic applications", ed. By C. G. Knight, Elsevier/North-Holland (1981), Chap. 3); and
(6) Liposome in life science, edited by Hiroshi Terada et al., Springer-Verlag, Tokyo.

Furthermore, the liposome of the present invention can be prepared, for example, by use of an ultrasonic dispersion method (direct dispersion method, cast thin-film formation method), a thermal dispersion method, an injection method, a cholic acid (surfactant) method (Proc. Natl. Acad. Sci. U.S.A., 76, 145 (1979), a freeze-thaw method (Arch. Biochim. Biophys., 212, 186 (1981)), a reverse-phase vaporization method (Proc. Natl. Acad. Sci. U.S.A., 75, 4194 (1978)), a giant liposome preparation method (Biochim. Biophys. Acta, 443, 629 (1976)), a vertical soaking method (LB method) ("surface", 26 295 (1988), Masatugu Shimomura," Oil chemistry", 39, 141 (1990)), a horizontal deposition method, a polyion complex forming method, and a method of encapsulating DNA into an aqueous phase within a liposome (Gene Ther 6, 271-281, 1999).

A method for preparing a lipid membrane structure further holding a gene or a nucleic acid, the following methods may be mentioned.
(i) A "complex method", in which a vacant cationic liposome is first prepared and then the liposome is simply mixed with an aqueous gene solution or an aqueous nucleic acid solution; and (ii) An method by "encapsulation type" in which a larger number of genes and nucleic acids and the like, are encapsulated in an aqueous phase within a liposome by various means and free cationic groups are allowed to remain outside the liposome.

As the latter method, the following methods may be mentioned (for examples, methods disclosed in WO 2005-032593 (Examples 1 and 2), Japanese Patent Laid-Open No. 2007-166946 (Example 1), and Journal of Biological Chemistry 281.6. (2006) 3544-3551).

(ii-1) A method of adding an aqueous gene solution or an aqueous nucleic acid solution directly to a vacant cationic liposome lyophilized.

(ii-2) A method in which a complex is formed between a cationic molecule, such as a polycationic peptide including polylysin and protamine, or a cationic lipid (including a phospholipid derivative (A)) for gene/nucleic acid introduction, and a gene or a nucleic acid, and thereafter, a gene or nucleic acid encapsulating liposome is prepared by a liposome membrane comprising no cationic lipid, and finally an aqueous cationic lipid solution is added, thereby allowing a cationic group to expose exclusively at the outside of a liposome particle.

(ii-3) Taking no consideration of an encapsulation efficiency of a gene and a nucleic acid, a gene or nucleic acid encapsulating liposome is first prepared from a liposome membrane comprising no cationic lipid. After removing a gene or nucleic acid not incorporated by a customary method, an aqueous cationic lipid solution is finally added, thereby allowing a cationic group to expose at the outside of the liposome particle.

The liposome of the present invention can be prepared by not only the methods described in Examples (later described) but also the following methods.

Example of a Process for Preparing a Liposome (1)

A liposome having a polycation site on the surface is prepared by a hydration method.

Phospholipid derivative (A) (about 0.75 mg) is dissolved in ethanol (about 9.0 mL).

Egg-yolk phosphatidyl choline (about 5.02 mg) and cholesterol (about 1.1 mg) are dissolved in chloroform (about 21 mL). Subsequently, both solutions are mixed and housed in a round-bottom flask (the final ratio of chloroform to ethanol=7:3). Subsequently, the solvent is evaporated by a rotatory evaporator and thereafter the residue is dried by housing it in a desiccator for 2 hours.

The obtained lipid membrane (10 μmol) is hydrated with a phosphate buffered saline solution (1 mL) previously warmed to 50° C. and stirred for 5 seconds. The lipid dispersion solution is passed through a membrane filter having a pore size of 400 nm, 200 nm or 100 nm, 11 times to prepare a liposome having a polycation site (5% by mole based on the total lipid) on the surface thereof. In this way, a vacant cationic liposome for use in the (a) "complex method" can be prepared.

Example of a Process for Preparing a Liposome (2)

A plasmid gene (about 8 μg) and a cation molecule (about 16 μg) (a phospholipid derivative (A), polylysin or protamine sulfate) are mixed in 10 mM HEPES buffer while stirring to prepare a complex of the plasmid gene and a phospholipid derivative (A), polylysin or protamine sulfate.

Separately, dioleoylphosphatidylethanolamine (about 0.672 mg) and cholesteryl hemisuccinate (about 0.096 mg) are dissolved in chloroform (about 1 mL). An aliquot (125 μL) is taken from the obtained solution and placed in a glass test tube. The solution is dried and solidified by spraying nitrogen gas to form a lipid membrane.

The complex containing solution (250 μL) is added to the lipid membrane and allowed to stand still at room temperature for 10 minutes to hydrate it. After the hydration, ultrasonic treatment is applied to the mixture for several seconds in an ultrasonic vessel to prepare a liposome encapsulating the above complex.

To the external solution of the liposome, about 12 μl of the 1 mg/mL phospholipid derivative (A) solution is added and allowed to stand still at room temperature for 30 minutes to prepare a liposome having a polycation site (5% by mole of the total lipid) on the surface thereof. In this way, a liposome for use in the (ii) "encapsulation method" (ii-2) can be prepared.

II) Production Method for a Micelle Comprising a Phospholipid Derivative (A)

A micelle-forming interface substance such as polyoxyethylene sorbitan fatty acid ester (Tween), a sodium fatty acid and polyoxyethylene is added to water at the concentration of a micelle forming critical concentration or more to prepare a micelle water-dispersion solution. To the prepared micelle water-dispersion solution, an aqueous solution of a phospholipid derivative (A) is added and allowed to stand still for a predetermined time, preferably warmed to 40° C. or more and then allowed to cool to produce a desired micelle containing the phospholipid derivative (A).

Furthermore, a micelle forming substance and a phospholipid derivative (A) can be previously mixed and then treated in accordance with a known micelle production method to also obtain a desired micelle.

III) Production Method for a Micro-Emulsion Containing a Phospholipid Derivative (A)

To the micelle comprising a phospholipid derivative (A) produced in accordance with the method II) above, fat and oil such as soybean oil is added and saturated the micelle with it. The oil phase is increased to the extent that an irreversible separation of the oil layer does not occur. In this manner, a desired micro-emulsion comprising the phospholipid derivative (A) can be produced.

Furthermore, to the micro-emulsion prepared in accordance with a known method, an aqueous phospholipid derivative (A) solution is added and allowed to stand still for a predetermined time, preferably warmed to 40° C. or more and then allowed to cool to also produce a desired micro-emulsion.

In the aforementioned production method for a lipid membrane structure, the type of lipid membrane structure to be produced can be varied by changing the ratio of a phospholipid derivative (A) of the present invention relative to the total lipid component.

If a lipid membrane structure (hereinafter sometimes referred to as the composition of the present invention) comprising a gene or a nucleic and the like is used, the gene or the nucleic acid can be efficiently introduced into a cell not only in-vitro but also in-vivo. More specifically, a gene and a nucleic acid can be introduced in a target cell in vitro by a means such as adding the composition of the present invention to a suspension solution containing the target cell or culturing the target cell in a medium containing the composition of the present invention. Furthermore, in vivo, the composition of the present invention may be administered to a host. As an administration means, oral administration and parenteral administration may be employed. As the dosage form for oral administration, a known dosage form may be mentioned and examples thereof include a tablet, powder and a granule. As the dosage form for parenteral administration, a known dosage form may be mentioned and examples thereof include an injection agent, an ophthalmic suspension, an ointment and a suppository. Preferably, parenteral administration is employed. Of them, an injection agent is preferable. As an administration method, systemic injection such as subcutaneous injection or local injection to a target cell and organ is preferable.

The compound to be applied to a lipid membrane structure of the present invention is not particularly limited; however, a medical drug having a very low lipid-solubility, a drug that is difficult to be introduced into a cell, such as a physiologically active peptide having a large molecular weight and a protein, a gene/nucleic acid may be applied. In particular, a gene/nucleic acid may be conceivably applied.

As the gene, either one of DNA and RNA may be used. Particularly, a gene to be introduced for, e.g., transduction in vitro, a gene that expresses in vivo to function such as a gene for use in a gene therapy such as a plasmid DNA, and a gene and the like, for producing iPS cells (induced pluripotent stem cells, artificial pluripotent stem cells) for use in breeding of industrial animals such as experimental animals and cattle, and regenerative medicine may be preferred. In the case where a gene encoding a certain type of enzyme, a substance expressing a pharmacological action by the action of the enzyme may be used in combination. For example, a tumor can be treated by allowing a thymidine kinase gene to express previously within a living body (tumor) by use of the composition of the present invention and then administering ganciclovir.

Examples of the nucleic acid include antisense medical drugs such as antisense DNA and antisense RNA, decoy oligo medical drugs such as a decoy oligo nucleic acid, or RNAi medical drug such as miRNA, shRNA and siRNA, Antagomir and RNAa (double stranded RNA molecule having a homologous sequence at the promoter site of a gene on a genome).

The use amount of the lipid membrane structure of the present invention is not particularly limited as long as it is sufficient to introduce gene/nucleic acid and the like into a cell. Such a use amount is preferably 0.1 to 100 parts by weight based on one part by weight of gene and the like, and more preferably 0.5 to 50 parts by weight.

EXAMPLES

The present invention will be more specifically described by way of Examples; however, the present invention is not limited to the Examples.

A phospholipid derivative (A) of the present invention can be produced, for example, by the methods described in Examples below. Furthermore, the effect of the phospholipid derivative (A) can be confirmed by the method described in the following experimental examples. However, these are just examples and the present invention is not limited in any cases by the specific examples below and may be modified within the range of the present invention.

A compound having a reference of a document name and the like, denotes that the compound was produced in accordance with the document and the like.

The following abbreviations in $^1$H-NMR measurement spectra mean as follows:
s: singlet
d: doublet
t: triplet
q: quartet
m: multiplet
br: broad
br, s: broad singlet

Production Example 1

Synthesis of Dilaurylphosphate

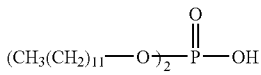

To a mixture of lauryl alcohol (15.227 g, 81.7 mmol) and benzene (50 ml), phosphorus oxychloride (2.5 ml, 26.8 mmol) was added dropwise at 80° C. (solvent reflux temperature) and further stirred for 21 hours. The solvent of the reaction solution was evaporated under a reduced pressure. To the obtained residue, hexane (10 ml) was added and cooled overnight. The precipitate generated was filtrated to obtain the titled compound (white powder, 4.12 g, 9.5 mmol, yield: 35%).

$^1$H-NMR (ppm) δ: 0.87-0.89 (t, 6H), 1.26-1.37 (br, s, 36H), 1.65-1.70 (m, 4H), 4.00-4.06 (m, 4H), 6.73 (br, s, 1H)

$^{13}$C-NMR (ppm) δ: 14.11, 22.69, 25.43, 29.17, 29.35, 29.53, 29.59, 29.64, 29.66, 30.15, 31.92, 67.68, 67.72

$^{31}$P-NMR (ppm) δ: 2.13

SIMS mass analysis:

Actual measurement value; 435.6

Theoretical value; 435.6 relative to (C24H52O4P)+

Production Example 2

Synthesis of Dilaurylphosphate Anhydride

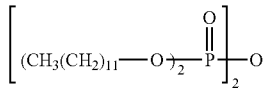

To a mixture of dilaurylphosphate (101 mg, 0.23 mmol) and anhydrous pyridine (0.8 ml) was added 1,3,5-triisopropylbenzene sulfonyl chloride (345 mg, 1.15 mmol). The reaction container was purged with nitrogen, and the mixture was stirred at room temperature for 3 hours. The solvent of the mixture was evaporated under a reduced pressure. The obtained residue was purified by silica gel column chromatography (eluant: chloroform) to obtain the target compound (77.2 mg, 0.09 mmol, yield: 78%).

$^1$H-NMR (ppm) δ: 0.88 (t, 12H), 1.26 (br, 64H), 1.37 (m, 8H), 1.70 (m, 8H), 4.0-4.2 (m, 8H)

$^{13}$C-NMR (ppm) δ: 14.11, 22.68, 25.36, 29.15, 29.35, 29.53, 29.59, 29.64, 29.66, 30.14, 31.91, 69.12

$^{31}$P-NMR (ppm) δ: −12.22, −12.20

MALDI-TOF mass analysis:

Actual measurement value; 852.03

Theoretical value; 852.23, relative to (C48H101O7P2)+

Production Example 3

Synthesis of Dimyristylphosphate

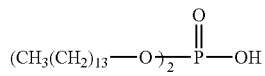

To a mixture of myristyl alcohol (17.25 g, 80.46 mmol) and benzene (50 ml), phosphorus oxychloride (2.5 ml, 26.8 mmol) was added dropwise at 80° C. (solvent reflux temperature) and further stirred for 20 hours. The solvent of the reaction solution was evaporated under a reduced pressure. To the obtained residue, hexane (10 ml) was added and cooled overnight. The precipitate generated was filtrated to obtain the titled compound (white powder, 1.56 g, 3.2 mmol, yield: 12%).

$^1$H-NMR (ppm) δ: 0.87-0.89 (t, 6H), 1.25-1.37 (br, s, 44H), 1.63-1.72 (m, 4H), 4.00-4.06 (m, 4H), 7.09 (br, s, 1H)

$^{13}$C-NMR (ppm) δ: 14.12, 22.69, 25.43, 29.18, 29.37, 29.54, 29.60, 29.67, 29.69, 29.70, 30.14, 30.19, 31.92, 67.75, 67.79

$^{31}$P-NMR (ppm) δ: 1.98

SIMS mass analysis:

Actual measurement value; 491.80

Theoretical value; 491.73, relative to (C28H60O4P)+

Production Example 4

Synthesis of Dimyristylphosphate Anhydride

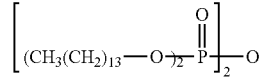

To a mixture of dimyristylphosphate (100 mg, 0.204 mmol) and anhydrous pyridine (0.7 ml) was added 1,3,5-triisopropylbenzene sulfonyl chloride (309 mg, 1.02 mmol). The reaction container was purged with nitrogen, and the mixture was stirred at room temperature for 2.5 hours. The solvent of the mixture was evaporated under a reduced pressure. The obtained residue was purified by silica gel column chromatography (eluant: chloroform) to obtain the target compound (73 mg, 0.09 mmol, yield: 75%).

$^1$H-NMR (ppm) δ: 0.88 (t, 12H), 1:25 (br, 80H), 1.37 (m, 8H), 1.70 (m, 8H), 4.00-4.20 (m, 8H)

$^{13}$C-NMR (ppm) δ: 14.11, 22.68, 25.36, 29.15, 29.36, 29.54, 29.60, 29.67, 29.69, 29.70, 30.14, 31.92, 69.12

$^{31}$P-NMR (ppm) δ: −12.22

MALDI-TOF mass analysis:

Actual measurement value; 986.12

Theoretical value; 986.42, relative to (C56H116O7P2Na)+

Production Example 5

Synthesis of Dicetylphosphate

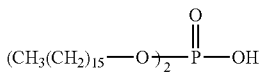

To a mixture of cetyl alcohol (19.50 g, 80.4 mmol) and benzene (100 ml), phosphorus oxychloride (2.5 ml, 26.8 mmol) was added dropwise at 80° C. (solvent reflux temperature) and further stirred for 12 hours. The solvent of the reaction solution was evaporated under a reduced pressure. To the obtained residue, benzene (50 ml) was added and cooled overnight. The precipitate generated was filtrated to obtain the titled compound (white powder, 1.64 g, 3.0 mmol, yield: 11%).

$^1$H-NMR (ppm) δ: 0.87-0.89 (t, 6H), 1.25-1.37 (br, s, 52H), 1.65-1.72 (m, 4H), 4.00-4.06 (m4H), 7.05 (br, s, 1H)

$^{13}$C-NMR (ppm) δ: 14.11, 22.69, 25.44, 29.18, 29.36, 29.54, 29.61, 29.66, 29.67, 29.70, 29.71, 30.16, 30.21, 31.93, 67.69, 67.73

$^{31}$P-NMR (ppm) δ: 2.15

SIMS mass analysis:

Actual measurement value; 547.85

Theoretical value; 547.83, relative to (C32H68O4P)+

Production Example 6

Synthesis of Dicetylphosphate Anhydride

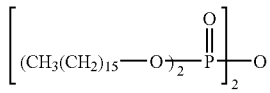

To a mixture of dicetylphosphate (50 mg, 90 μmol) and anhydrous pyridine (1 ml) was added 1,3,5-triisopropylbenzene sulfonyl chloride (277 mg, 0.91 mmol). The reaction container was purged with nitrogen, and the mixture was stirred at room temperature for 3 hours. The solvent of the mixture was evaporated under a reduced pressure. The obtained residue was purified by silica gel column chromatography (eluant:chloroform) to obtain a target compound (44.3 mg, 41 μmol, yield: 90%).

Element analysis:

Actual measurement value; C71.49, H12.32

Theoretical value; C71.46, H12.37 (C64H132O7P2)

$^1$H-NMR (ppm) δ: 0.88 (t, 12H), 1.25 (br, 96H), 1.37 (m, 8H), 1.70 (m, 8H), 4.00-4.20 (m, 8H)

$^{13}$C-NMR (ppm) δ: 14.01, 22.68, 25.36, 25.45, 29.16, 29.36, 29.54, 29.60, 29.66, 29.71, 30.31, 31.92, 67.67, 69.12

$^{31}$P-NMR (ppm) δ: −12.27, −0.13

SIMS mass analysis:

Actual measurement value; 1075.4

Theoretical value; 1075.9, relative to (C64H133O7P2)+

Production Example 7

Synthesis of N-[3-(2-pyridylthio)propionyl]-1,2-dipalmitoyl-sn-glycero-phosphoethanolamine

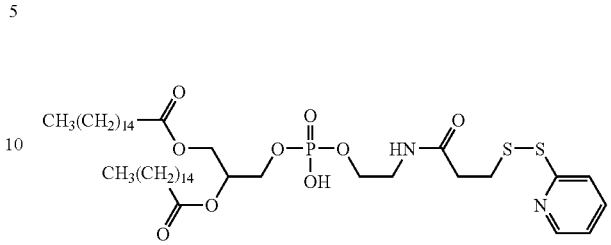

To a mixture of (N-succinimidyl-3-(2-pyridyldithio)propionate (SPDP) (21.9 mg, 0.0701 mmol) and chloroform (0.5 ml), after a flask is purged with argon, were added a mixture of chloroform (2 ml) and 1,2-dipalmitoyl-sn-glycero-phosphoethanolamine (DPPE: 40.7 mg, 0.0588 mmol) and a triethylamine (0.01 ml). The mixture was stirred at 40° C. for 21 hours under an argon atmosphere. The solvent of the reaction solution was evaporated under a reduced pressure. The obtained residue was purified by preparative thin-film chromatography (eluant: chloroform/methanol/water=13/6/1, Rf=about 0.6-0.7 partition was isolated) to obtain the titled compound (46 mg, 0.052 mmol, yield: 88%).

$^1$H-NMR (ppm) δ: 0.85-0.90 (t, 6H), 1.08-1.32 (br, 48H), 1.52-1.55 (m, 4H), 2.23-2.30 (m, 4H), 2.63-2.67 (br, 2H), 3.01-3.08 (br, 2H), 3.46 (s, 2H), 3.88-3.92 (br, s, 4H), 4.11-4.17 (m, 1H), 4.36 (d, 1H), 5.22 (s, 1H), 7.05 (m, 1H), 7.62 (m, 2H), 7.81 (br, s, 1H), 8.42 (m, 1H)

MALDI-TOF mass analysis:

Actual measurement value; 933.5

Theoretical value; 933.5, relative to (C45H80O9N2PS2Na2)+

Production Example 8

Synthesis of N-(4-maleimidebutyloxy)-1,2-dipalmitoyl-sn-glycero-phosphoethanolamine

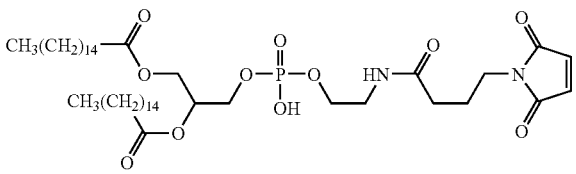

To a mixture of N-(4-maleimidebutyloxy)succinimide (9.7 mg, 0.0347 mmol) and chloroform (0.5 ml), after a flask is purged with argon, were added a mixture of chloroform (2 ml) and 1,2-dipalmitoyl-sn-glycero-phosphoethanolamine (DPPE: 20 mg, 0.0289 mmol) and triethylamine (0.01 ml). The mixture was stirred at room temperature for 4 hours under a nitrogen atmosphere. The solvent of the reaction solution was evaporated under a reduced pressure. The obtained residue was purified by silica gel chromatography (eluant: (1) chloroform (for eluting a by-product and unreacted compounds; (2) chloroform/methanol/water=13/6/1 (for eluting a desired product)). The solvent of the eluate was evaporated under a reduced pressure and further by a vacuum pump to obtain the titled compound (white solid, 21.3 mg, yield: 86%).

$^1$H-NMR (ppm) δ: 0.85-0.90 (t, 6H), 1.19-1.41 (m, 48H), 1.47-1.63 (m, 4H), 1.83-2.02 (m, 2H), 2.20-2.39 (m, 6H), 3.39-3.49 (m, 2H), 3.49-3.62 (m, 2H), 3.82-4.02 (m, 4H), 4.09-4.18 (m, 1H), 4.36-4.42 (d, 1H), 5.18-5.22 (s, 1H), 6.65-6.80 (s, 2H).

MALDI-TOF mass analysis:
Actual measurement value; 858.3
Theoretical value; 858.1, relative to (C45H82O11N2P)+

Example 1

Synthesis of Phospholipid Derivative (P-1)

The phospholipid derivative, which is a compound represented by the above general formula (1), wherein $R^1$ and $R^2$ each are a hexadecyl group, $Z^1$ and $Z^2$ each are a 1,2-ethylene group (—CH$_2$—CH$_2$—) and $Z^3$ is a hydrogen atom.

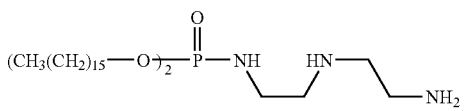

To a mixture of diethylenetriamine (19.17 mg, 0.186 mmol) and anhydrous pyridine (0.5 ml) was added a mixture of dicetylphosphate anhydride (40 mg, 0.037 mmol) and anhydrous pyridine (0.4 ml). The reaction container was purged with nitrogen and the mixture was stirred at room temperature for 2 hours to carry out a reaction. After the solvent of the mixture was evaporated, purification was carried out by silica gel column chromatography (eluant: (1) a mixture of chloroform/methanol/triethylamine=10/1/0.1 (volume ratio) for eluting a by-product; (2) a mixture of chloroform/methanol/triethylamine=10/1/0.1 (volume ratio) for eluting a desired product). The solvent of the eluate was evaporated under a reduced pressure and further by a vacuum pump to obtain the titled compound (white solid, 15.3 mg, yield: 65%).

$^1$H-NMR (ppm) δ: 0.88 (t, 6H), 1.26 (s, 48H), 1.35 (m, 4H), 1.66 (m, 4H), 1.81 (br, 4H), 2.68-2.83 (m, 5H), 3.00 (m, 2H), 3.25 (br, 1H), 3.98 (m, 4H)

$^{13}$C-NMR (ppm) δ: 14.11, 22.68, 25.61, 29.23, 29.36, 29.56, 29.60, 29.65, 29.70, 30.38, 30.43, 31.92, 41.01, 41.53, 50.13, 66.41, 66.44

$^{31}$P-NMR (ppm) δ: 9.78, 9.81
MALDI-TOF mass analysis:
Actual measurement value; 632.59
Theoretical value; 632.99 relative to (C36H79N3O3P)+

Example 2

Synthesis of Phospholipid Derivative (P-2)

The phospholipid derivative, which is a compound represented by the above general formula (1), wherein $R^1$ and $R^2$ each are a hexadecyl group, $Z^1$ and $Z^2$ each are a 1,3-propylene group and $Z^3$ is a hydrogen atom.

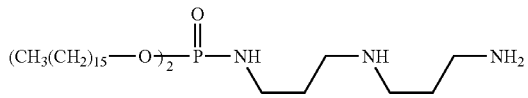

To a mixture of dipropylenetriamine (11.2 mg, 0.0854 mmol) and anhydrous pyridine (0.5 ml) was added a mixture of dicetylphosphate anhydride (16.5 mg, 0.0153 mmol) and anhydrous pyridine (0.5 ml). The reaction container was purged with nitrogen and the mixture was stirred at room temperature for 3 hours to carry out a reaction. After the solvent of the mixture was evaporated, purification was carried out by silica gel column chromatography (eluant: (1) a mixture of chloroform/methanol/triethylamine=10/1/0.1 (volume ratio) for eluting a by-product; (2) a mixture of chloroform/methanol/triethylamine=1/1/0.15 (volume ratio) for eluting a desired product. The solvent of the eluate was evaporated under a reduced pressure and further by a vacuum pump to obtain the titled compound (white solid, 7.7 mg, yield: 78%).

$^1$H-NMR (ppm) δ: 0.88 (t, 6H), 1.26 (s, 48H), 1.33 (bm, 4H), 1.65 (br, m, 4H), 1.85-2.02 (m, 4H), 2.83-3.08 (br, m, 12H), 3.91-4.01 (m, 4H)

MALDI-TOF mass analysis:
Actual measurement value; 661.0
Theoretical value; 661.0, relative to (C38H83N3O3P)+

Example 3

Synthesis of Phospholipid Derivative (P-3)

The phospholipid derivative, which is a compound represented by the above general formula (1), wherein $R^1$ and $R^2$ each are a hexadecyl group, $Z^1$ and $Z^2$ each are a 1,2-ethylene group and $Z^3$ is —CH$_2$CH$_2$—NH$_2$.

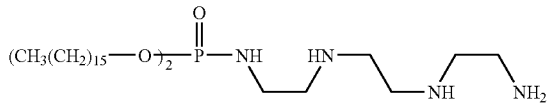

To a mixture of triethylenetetraamine (343.9 mg, 2.35 mmol) and anhydrous pyridine (1.0 ml) were added a mixture of dicetylphosphate anhydride (474.9 mg, 0.441 mmol) and anhydrous pyridine (2 ml). The reaction container was purged with nitrogen and the mixture was stirred at room temperature for 4 hours to carry out a reaction. After the solvent of the mixture was evaporated, the mixture was washed with distilled water. The residue washed was purified by silica gel column chromatography (aminated silica gel, eluant: (1) a mixture of chloroform/methanol=39/1 (volume ratio) for eluting a desired product). The solvent of the eluate was evaporated under a reduced pressure and further by a vacuum pump to obtain the titled compound (white solid, 197.7 mg, yield: 67%).

$^1$H-NMR (ppm) δ: 0.88 (t, 6H), 1.26 (s, 48H), 1.36 (m, 4H), 1.66 (m, 4H), 1.80 (br, s, 5H), 2.65-3.24 (m, 12H), 3.97 (m, 4H)

$^{31}$P-NMR (ppm) δ: 9.79
FAB mass analysis:
Actual measurement value; 697.5
Theoretical value; 698.0, relative to (C38H83N4O3PNa)+

Example 4

Synthesis of Phospholipid Derivative (P-4)

The phospholipid derivative, which is a compound represented by the above general formula (1), wherein $R^1$ and $R^2$ each are a hexadecyl group, $Z^1$ and $Z^2$ each are a 1,2-ethylene group and $Z^3$ is —$CH_2CH_2$—NH—$CH_2CH_2$—$NH_2$.

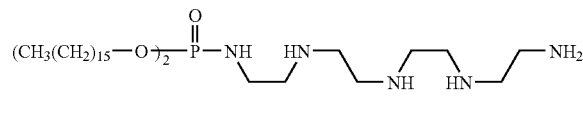

To a mixture of tetraethylenepentaamine (351.0 mg, 1.85 mmol) and anhydrous pyridine (2 ml) were added a mixture of dicetylphosphate anhydride (322.4 mg, 0.299 mmol)) and anhydrous pyridine (3 ml). The reaction container was purged with nitrogen and the mixture was stirred at room temperature for 4 hours. After the solvent of the mixture was evaporated, the mixture was washed with distilled water. The residue washed was purified by silica gel column chromatography (aminated silica gel, eluant: (1) a mixture of chloroform/methanol=39/1 (volume ratio) for eluting a desired product). The solvent of the eluate was evaporated under a reduced pressure and further by a vacuum pump to obtain the titled compound (white solid, 77.3 mg, yield: 36%).

$^1$H-NMR (ppm) δ: 0.88 (t, 6H), 1.25 (s, 48H), 1.36 (m, 4H), 1.66 (m, 4H), 1.75 (br, s, 6H), 2.35-3.35 (br, m, 16H), 3.97 (m, 4H)

MALDI-TOF mass analysis:

Actual measurement value; 718.2

Theoretical value; 718.7, relative to (C40H89N5O3P)+

Example 5

Synthesis of Phospholipid Derivative (P-5)

The phospholipid derivative, which is a compound represented by the above general formula (2), wherein $Y^3$ and $Y^4$ each are a carbonyl group, $R^3$ and $R^4$ each are a pentadecyl group, $T^1$ is represented by the aforementioned formula T2, and n is 5 (a compound represented by the formula below).

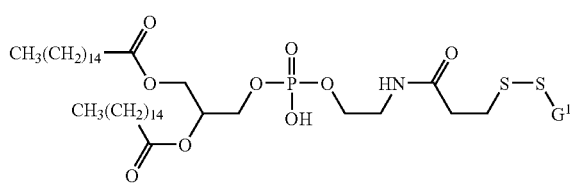

wherein G1 is represented by

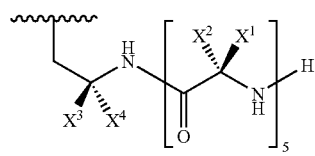

wherein $X^1$ to $X^4$ are the same as defined above.

To a mixture of N-[3-(2-pyridylthio)propionyl]-1,2-dipalmytoyl-sn-glycro-phosphoethanolamine (8.1 mg, 9.1 μmol) and a solution mixture of chloroform, methanol and water (chloroform/methanol/water=13/6/1 (volume ratio), 0.4 ml) was added a mixture of a peptide (Arg-Arg-Arg-Arg-Arg-Cys (the left side is the N terminal, both Arg and Cys of the peptide are L-form, hereinafter sometimes referred to as RRRRRC) (6.83 mg, 7.37 μmol) and a solution mixture of chloroform/methanol/water (chloroform/methanol/water=13/6/1 (volume ratio), 0.2 ml). The reaction container was purged with argon, and the mixture was stirred at room temperature for 3 hours to carry out a reaction. After the solvent of the mixture was evaporated under a reduced pressure, purification was carried out by silica gel column chromatography (aminated silica, eluant: (1) a mixture of chloroform/methanol/water=13/6/1 (volume ratio) for removing a by-product and an unreacted compounds, and (2) a mixture of chloroform/methanol/acetic acid for eluting a desired product). After the solvent of the eluate was evaporated under a reduced pressure, chloroform was added. The chloroform solution (chloroform layer) was washed with an aqueous sodium hydrogen carbonate solution. After the chloroform layer was dried, the solvent in the chloroform layer was evaporated under a reduced pressure and further by a vacuum pump to obtain the titled compound (white solid, 1.1 mg, yield: 10%).

MALDI-TOF mass analysis:

Actual measurement value; 1680.83

Theoretical value; 1680.03, relative to (C73H144N22O16PS2)+

Example 6

Synthesis of Phospholipid Derivative (P-6)

The phospholipid derivative, which is a compound represented by the above general formula (2), wherein $Y^3$ and $Y^4$ each are a carbonyl group, $R^3$ and $R^4$ each are a pentadecyl group, $T^1$ is represented by the aforementioned formula T3, and n is 5 (a compound represented by the formula below).

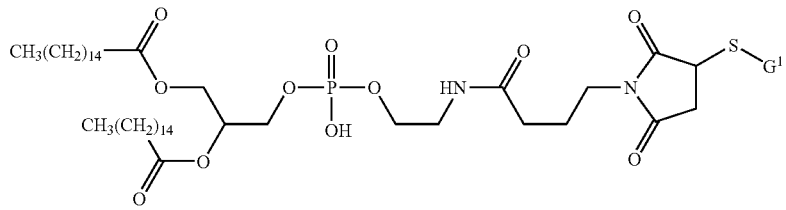

wherein G1 is the same as defined in $G^1$ of Example 5.

A mixture of N-(4-maleimidebutyloxy)-1,2-dipalmitoyl-sn-glycero-phosphoethanolamine (5.0 mg, 0.00584 mmol) and a solution mixture of chloroform, methanol and water (chloroform/methanol/water=13/6/1 (volume ratio), 0.5 ml) was added dropwise to a mixture of a peptide (RRRRRC, 7.3 mg, 0.00813 mmol) and a solution mixture of chloroform/methanol/water (chloroform/methanol/water=13/6/1 (volume ratio), 2 ml). The reaction container was purged with nitrogen, and the mixture was stirred at room temperature for 29 hours. To the mixture, a mixture of ammonium acetate (32.7 mg, 0.424 mmol) and methanol (1.5 ml) was added and stirred at room temperature for 12 hours. The solvent of the mixture was evaporated under a reduced pressure. To the residue, methanol (10 µl) was added and further chloroform was added. The chloroform solution (chloroform layer) was washed with an aqueous ammonium acetate solution. After the chloroform layer was dried, the solvent in the chloroform layer was evaporated under a reduced pressure and further by a vacuum pump to obtain the titled compound (white solid, 8.8 mg, yield: 74%).

FAB mass analysis:
Actual measurement value; 1759.88
Theoretical value; 1760.20, relative to $(C78H149N23O18PS)+$ Experimental Example B1

Liposome Comprising a Phospholipid Derivative (P-1) (Introduction of Plasmid DNA)

Preparation of a liposome comprising a phospholipid derivative (P-1) and evaluation of gene introduction efficiency (fluorescent intensity) of the liposome.

B1-1: Preparation of Liposome

A lipid (a phospholipid derivative (P-1)/dioleoylphosphatidylethanolamine/cholesterol=1/1/1 (molar ratio)) was taken by a micro syringe and an appropriate amount of tert-butanol was added. After sufficiently stirred, the mixture was lyophilized overnight. To the resultant lyophilized lipid powder, a Tris-HCL solution warmed to 60° C. was added and completely condensated while using a vortex mixer. The resultant mixture was passed through a polycarbonate membrane filter of 100 nm in pore size set at an extruder 10 times to control the particle size of liposomes.

B1-2. Cell Culture

As Cells, COS-1 cells were used. The cells were stored in a Dulbecco's modified Eagle medium solution [a solution containing 10% fetal bovine serum (FBS) and kanamycin (60 µg/mL)] at 37° C. in the presence of 5% carbon dioxide. Cells, when reached a confluent state, were removed by a 0.175% trypsin/EDTA-PBS (−) solution.

B1-3. Evaluation of Transfection

Twenty four hours before transfection, the cultured cells as mentioned above were placed in a culture dish of 35 mm in diameter. A luciferase plasmid DNA (pCAG-luc3) solution and the solution containing the liposome prepared in the above step (B1-1) were mixed to prepare a complex comprising nitrogen derived from the above (B1-1) liposome and phosphorus derived from the plasmid DNA in a charge ratio of 24:1. After the complex was incubated at room temperature for 20 minutes, the complex corresponding to 1 µg of the plasmid DNA was added to a cell medium. Three hours after addition of the complex, the medium was exchanged. Forty eight hours after addition of the complex, a transfection evaluation test was carried out. The culture solution was removed from the culture dish, the cells were washed twice with a PBS solution, and 200 µL of a buffer solution (LCβ) for lysis was added to lyse the cells. The cell lysis solution was collected in a 1.5 mL Eppendorf tube, frozen and thawed. Thereafter, the tube was subjected to centrifugal separation carried out at 21,500 g for 10 minutes. The supernatant was recovered and transferred to a tube for measurement. To the tube, an emission substance was added and luciferase activity was measured by a lumino-photometer (Luminescencer-PSN AB 2200, ATTO Corporation). The luminescence intensity of each sample was corrected based on the mass of a protein.

B1-4. Results

The results are shown in FIG. 1 and Table 2. The transfection efficiency was evaluated using emission intensity as a reference. It is meant that the larger the emission amount is, the higher the transfection efficiency is.

In FIG. 1, the vertical axis shows the emission amount per protein (1 mg) and employs a relative light unit (RLU)/mg, as the unit.

In FIG. 1 and Table 2, "(B1-1)" represents a liposome prepared in the above step (B1-1); "LFK2K" represents a liposome prepared by mixing Lipofectamine 2000 and the plasmid DNA of the above step (B1-1); and "DCP-spermidine PCL" represents a liposome prepared using a compound containing spermidine (CAS. No. 730979-01-8) in the same manner as in the step (B1-1).

TABLE 2

| liposome | RLU/mg proein |
| --- | --- |
| (B1-1) | 1.25E+11 |
| DCP-spermidine PCL | 1.83E+10 |
| LFK2K | 1.68E+10 |

The liposome (the above step (B1-1)) comprising a phospholipid derivative (P-1) exhibited a high gene introduction efficiency compared to DCP-spermidine PCL and commercially available nucleic acid introducing reagent Lipofectamine 2000 (Invitrogen Corporation).

Experimental Example B2

Liposome Comprising a Phospholipid Derivative (P-1) (siRNA)

Preparation of a liposome comprising a phospholipid derivative (P-1) and evaluation of gene introduction efficiency (gene knockdown efficiency) of the liposome B2-1. Preparation of Liposome A lipid (a phospholipid derivative (P-1)/dioleoylphosphatidylethanolamine/cholesterol/distearoylphos phatidylethanolamine-polyethylene glycol 2000-peptide (alanine-proline-arginine-proline-glycine)=1/1/1/0.75 (molar ratio)) was taken by a micro-syringe and isopropanol was added thereto up to a total amount of 1 mL. On the other hand, siRNA (150 pmol) capable of knocking down GAPDH was dissolved in DEPC treated water to obtain a total amount of 0.5 mL. The siRNA solution was added to the lipid mixture solution and incubated for 20 minutes. Subsequently, the DEPC treated water (5 mL) was added dropwise little by little with stirring while keeping the temperature at 60° C. The resultant solution was transferred to an ultrafiltration appliance (Amicon Ultra (100 k)). Exchange of solvent and concentration operation were carried out to obtain an siRNA-comprising liposome.

B2-2. Cell Culture

As cells, human umbilical vein endothelial cells (HUVEC) were used. The cells were stored in a solution of endothelial basal medium-2 (EGM-2, Bio Whittaker Inc.) at 37° C. in the presence of 5% carbon dioxide. When the cells reached a confluent state, the cells were removed with a 0.025 mg/mL trypsin/EDTA-PBS (−) solution.

B2-3. Evaluation of Gene Knockdown

Sixteen hours before transfection, the cultured cells as mentioned above were placed in a culture dish of 35 mm in diameter. The siRNA solution (Hokkaido System Science Co., Ltd.) capable of knocking down GAPDH and the solution containing the liposome prepared in the above step (B2-1) were separately diluted with DEPC treated water and incubated at room temperature for 5 minutes. The siRNA solution was mixed with the solution containing the liposome prepared in the above step (B2-1) in the same volume to obtain a complex comprising nitrogen derived from the (B2-1) liposome and phosphorus derived from siRNA in a charge ratio of 24/1. After the complex was incubated at room temperature for 20 minutes, it was added to a cell medium so as to obtain a final siRNA concentration of 50 nM. Twenty four hours after the addition of the complex, the medium was exchanged. Forty eight or seventy two hours after the addition of the complex, gene knockdown was evaluated. The culture solution was removed from the culture dish and the cells were washed once with a PBS solution and lysed by adding 200 µL of a lysis buffer solution [a 1% reduced triton X-100 solution containing 2 mM phenylmethylsulfonyl fluoride (PMSF), 0.2 mM leupeptin, 0.05 mg/mL aprotinin and 0.1 mM pepstatin A]. The cell lysis solution was collected in a 0.5 mL Eppendorf tube and stored at −20° C. Each sample was separated by SDS-PAGE and the amount of GAPDH was detected by the Western blotting method. As a color emitting reagent, ECL Western blotting detection regents (GE Healthcare) were used and detection was carried out by LAS3000 (Fuji Film Corporation) to obtain a numerical value.

B2-4. Results

Figure 2:
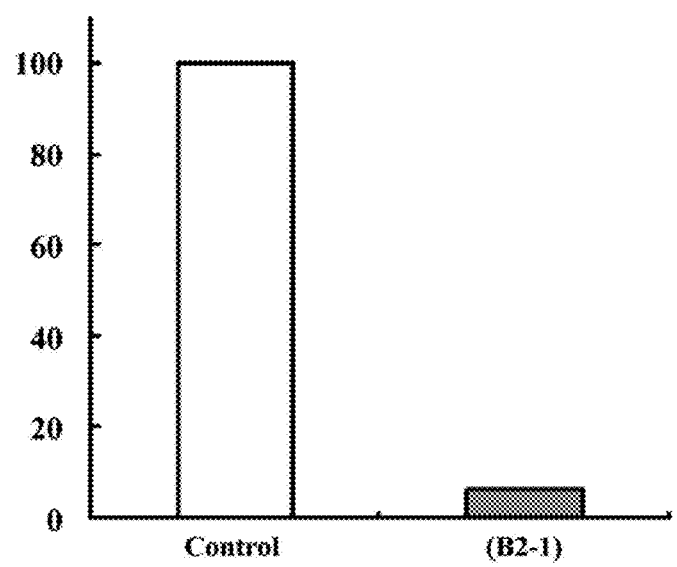
FIG. 2 shows results of gene knockdown evaluation in Experimental Example B2.

The results are shown in FIG. 2 and Table 3. Gene knockdown was evaluated based on reduction of protein expression as a reference. The smaller the value in the graph is, the higher the gene knockdown efficiency is. In short, this means that gene introduction efficiency is high.

In FIG. 2, the vertical axis shows the protein expression amount when the protein expression amount of a control is regarded as 100.

The "(B2-1)" in FIG. 2 and Table 3 represents the liposome prepared in the above step (B2-1).

TABLE 3

| Control | (B2-1) |
|---------|--------|
| 100.0   | 5.9    |

When GAPDH was knocked down by using the liposome (the above step (B2-1)) comprising a phospholipid derivative (P-1), expression suppression efficiency of about 94% was obtained.

Experimental Example B3

Liposome Comprising a Phospholipid Derivative (P-1) (In-Vivo Pharmacokinetics of siRNA)

Preparation of a liposome comprising a phospholipid derivative (P-1) and evaluation of siRNA transfer into a cancer tissue using the liposome B3-1. Preparation of Liposome A lipid (a phospholipid derivative (P-1)/dioleoylphosphatidylethanolamine/cholesterol/distearoylphos phatidylethanolamine-polyethylene glycol 2000-peptide (alanine-proline-arginine-proline-glycine)=1/1/1/0.75 (molar ratio)) was taken by a micro-syringe and isopropanol was added thereto up to a total amount of 1 mL. Subsequently, an siRNA solution (0.5 mL) labeled with ALexa 750 was added to the lipid mixture solution and incubated for 20 minutes. Then, the DEPC treated water (5 mL) was added dropwise little by little with stirring while keeping the temperature at 60° C. The resultant solution was transferred to an ultrafiltration appliance (Amicon Ultra (100 k)). Exchange of solvent and concentration operation were carried out to obtain an siRNA-comprising liposome.

B3-2. Cell Culture

As cells, mouse Colon 26 NL-17 carcinoma cells were used. The cells were stored in a solution of DME/HamF12 medium [a solution containing 10% fetal bovine serum (FBS), penicillin G (60 µg/mL) and streptomycin (100 µg/mL] at 37° C. in the presence of 5% carbon dioxide. When the cells reached a confluent state, the cells were removed with a 0.25% Trypsin/EDTA-PBS (−) solution and subcultured.

B3-3. Production of Cancer-Bearing Animal

Colon 26 NL-17 carcinoma cells ($1 \times 10^6$ cells) were subcutaneously transplanted in the outer side of a mouse left leg. Ten days after the transplantation, in vivo pharmacokinetics were evaluated.

The liposome prepared in the above step (B3-1) was administered to the caudate vein of a cancer-bearing mouse in an amount of 30 µg in terms of siRNA. The in-vivo pharmacokinetics of siRNA were measured and visualized by the IVIS Lumina Imaging System (Xenogen Corporation).

B3-4. Results

Figure 3:
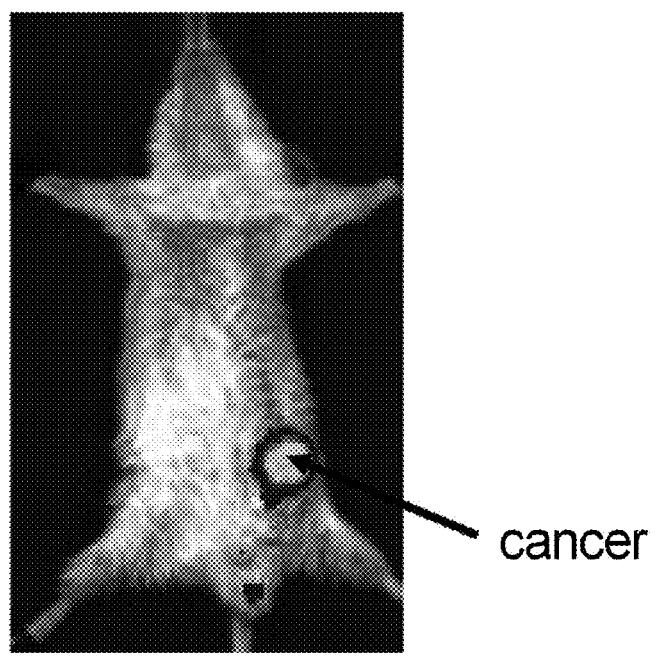
FIG. 3 shows the distribution of siRNA 24 hours after administration in Experimental Example B3.

The distribution of siRNA 24 hours after administration is shown in FIG. 3.

It was found that siRNA is migrated into cancer cells with high selectivity by use of the liposome (the above step (B3-1)) comprising a phospholipid derivative (P-1).

Experimental Example 84

Liposome (siRNA) Comprising a Phospholipid Derivative (P-1) or a Phospholipid Derivative (P-4)

Preparation of liposome comprising a phospholipid derivative (P-1) or a phospholipid derivative (P-4), and evaluation of gene introduction efficiency (reduction of fluorescent intensity by knockdown) of the liposome B4-1. Preparation of Liposome A lipid (a phospholipid derivative (P-1)/dioleoylphosphatidylethanolamine/cholesterol/=1/1/1 (molar ratio)) or (a phospholipid derivative (P-4)/dioleoylphosphatidylethanolamine/cholesterol/=1/1/1 (molar ratio)) was taken by a micro-syringe and an appropriate amount of tert-butanol was added thereto. After stirring well, the mixture was lyophilized overnight. To the resultant lyophilized lipid powder, DEPC treated water warmed to 60° C. was added and completely condensated while using a vortex mixer. The resultant mixture was passed through a polycarbonate membrane filter of 100 nm in pore size set at an extruder 10 times to control the particle size of liposomes.

B4-2. Cell Culture

As cells, HT1080 human fibroblastic sarcoma cells (EGFP/HT1080 cells) constantly expressing enhanced green fluorescent protein (EGFP) were used. The cells were stored in a DME/HamF12 medium solution [the solution containing 10% fetal bovine serum (FBS) and penicillin G (60 μg/mL) and streptomycin (100 μg/mL)] at 37° C. in the presence of 5% carbon dioxide. Cells, when reached a confluent state, were removed by a 0.25 mg/mL trypsin/EDTA-PBS (−) solution.

B4-3. Evaluation of Gene Knockdown

Sixteen hours before transfection, the cultured cells as mentioned above were placed in a plate having 24 wells. The siRNA solution (Hokkaido System Science Co., Ltd.) capable of knocking down EGFP and the liposome solution prepared in the above step (B4-1) were separately diluted with DEPC treated water and incubated at room temperature for 5 minutes. The siRNA solution was mixed with the liposome solution prepared in the above step (B4-1) in the same volume to obtain a complex containing nitrogen derived from the liposome solution prepared in the above step (84-1) and phosphorus derived from siRNA in a charge ratio of 24/1. After the complex was incubated at room temperature for 20 minutes, it was added to a cell medium so as to obtain a final siRNA concentration of 50 nM. Four or twenty four hours after the addition of the complex, the medium was exchanged. Forty eight or seventy two hours after the addition of the complex, gene knockdown was evaluated. The culture solution was removed from each of the wells of the plate and the cells were washed once with a PBS solution and lysed by adding 200 μL of a lysis buffer solution [a 1% reduced triton X-100 solution containing 2 mM phenylmethylsulfonyl fluoride (PMSF), 0.2 mM leupeptin, 0.05 mg/mL aprotinin and 0.1 mM pepstatin A]. The cell lysis solution was collected in a 1.5 mL Eppendorf tube, centrifuged at 1000 g for 10 minutes and the supernatant was collected. The fluorescent intensity of the sample was measured by a fluorometer (1420 MULTILABEL COUNTER, WALLAC, ARVO™SX). The fluorescent intensity of each sample was corrected based on the mass of a protein.

B4-4. Results

Figure 4:
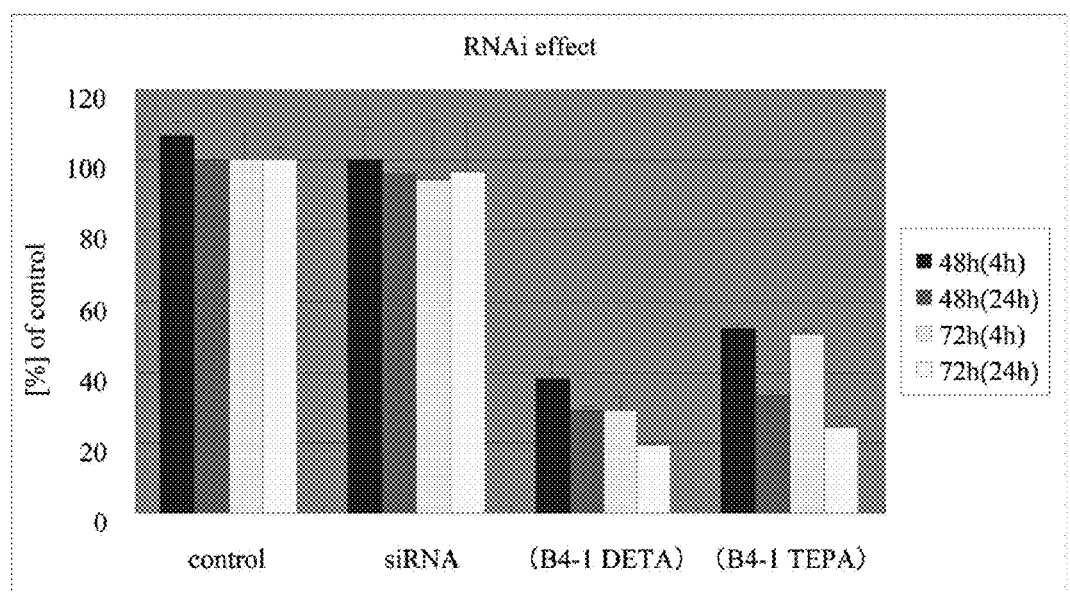
FIG. 4 shows results of gene knockdown evaluation in Experimental Example B4.

The results are shown in FIG. 4 and Table 3.

Gene knockdown was evaluated based on reduction of fluorescent intensity as a reference. It is meant that the smaller the fluorescent intensity is, the higher the gene knockdown efficiency is.

In FIG. 4, the vertical axis shows the value when the fluorescent intensity of a control is regarded as 100. Four graphs respectively show evaluation results of 48 h (4 h), 48 h (24 h), 72 h (4 h) and 72 h (24 h) from the left.

In FIG. 4 and Table 4, numerical values without parentheses represent the time at which gene knockdown was evaluated; whereas numerical values with parentheses represent the time at which the medium was exchanged. In each sample, the time at which a complex is added represents 0. Accordingly, for example, 72 h (24 h) represents that the gene knockdown evaluation was carried out 72 hours later and the medium was exchanged 24 hours later.

In FIG. 4 and Table 4, "siRNA" represents that the same amount of siRNA as in that of other experiments was administered without using a liposome. In FIG. 4 and Table 4, "(B4-1 DEPA)" represents the liposome prepared in the above step (B4-1) using a phospholipid derivative (P-1); whereas, "(B4-1 TEPA)" represents the liposome prepared in the above step (B4-1) using a phospholipid derivative (P-4).

TABLE 4

|            | 48 h (4 h) | 48 h (24 h) | 72 h (4 h) | 72 h (24 h) |
|------------|------------|-------------|------------|-------------|
| control    | 100.0      | 100.0       | 100.0      | 100.0       |
| siRNA      | 93.7       | 96.2        | 94.3       | 96.9        |
| (B4-1 DETA)| 35.8       | 29.1        | 28.9       | 19.6        |
| (B4-1 TEPA)| 49.1       | 33.8        | 50.7       | 24.7        |

Each of the liposome (the above step (B4-1)) comprising a phospholipid derivative (P-1) or a phospholipid derivative (P-4) exhibited high gene knockdown effect in cancer cells.

Experimental Example B5

Liposome (siRNA) Comprising a Phospholipid Derivative (P-1) or a Phospholipid Derivative (P-4)

Evaluation of gene introduction efficiency (reduction of protein (GAPDH) expression) of a liposome comprising a phospholipid derivative (P-1) or a phospholipid derivative (P-4)

B5-1. Preparation of Liposome

Liposome that can be prepared in the above step (B4-1) was used.

B5-2. Cell Culture

As cells, human umbilical vein endothelial cells (HUVEC) were used. The cells were stored in the endothelial basal medium-2 (EGM-2, Bio Whittaker Inc.) solution at 37° C. in the presence of 5% carbon dioxide. Cells, when reached a confluent state, were removed by a 0.025 mg/mL trypsin/EDTA-PBS (−) solution.

B5-3. Evaluation of Gene Knockdown

Sixteen hours before transfection, the cells cultured above were placed in a culture dish of 35 mm in diameter. The siRNA solution (Hokkaido System Science Co., Ltd.) capable of knocking down GAPDH and the liposome solution prepared in the above step (B4-1) were separately diluted with DEPC treated water and incubated at room temperature for 5 minutes. The siRNA solution was mixed with the liposome solution prepared in the above step (B4-1) in the same volume to obtain a complex containing nitrogen derived from the liposome solution prepared in the above step (B4-1) and phosphorus derived from siRNA in a charge ratio of 24/1. After the complex was incubated at room temperature for 20 minutes, it was added to a cell medium so as to obtain a final siRNA concentration of 50 nM. Twenty four hours after the addition of the complex, the medium was exchanged. Forty eight or seventy two hours after the addition of the complex, gene knockdown was evaluated. The culture solution was removed from the culture dish and the cells were washed once with a PBS solution and lysed by adding 200 μL of a lysis buffer solution [a 1% reduced triton X-100 solution containing 2 mM phenylmethylsulfonyl fluoride (PMSF), 0.2 mM leupeptin, 0.05 mg/mL aprotinin and 0.1 mM pepstatin A]. The cell lysis solution was collected in a 0.5 mL Eppendorf tube and stored at −20° C. Each sample was separated by SDS-PAGE and the GAPDH amount was detected by the WESTERN blotting method. As a color emitting reagent, ECL Western blotting detection regents (GE Healthcare) were used and detection was carried out by LAS3000 (Fuji Film Corporation).

B5-3. Results

Figure 5:
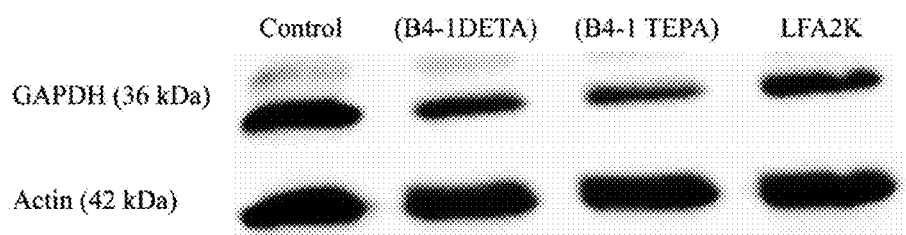
FIG. 5 shows results gene knockdown evaluation in Experimental Example B5.

The results are shown in FIG. 5.

Gene knockdown was evaluated based on reduction of protein expression as a reference. It is meant that the thinner the band is, the higher the gene knockdown efficiency is.

In FIG. 5, the "(B4-1 DETA)" represents the liposome prepared in the above step (B4-1) using a phospholipid derivative (P-1) and the "(B4-1 TEPA)" represents the liposome prepared in the above step (B4-1) using a phospholipid derivative (P-4). "LFA2K" represents the liposome prepared by mixing siRNA and Lipofectamine 2000 and incubating the mixture at room temperature for 20 minutes and adding the mixture to a cell medium so as to obtain a final siRNA concentration of 50 nM.

The liposome (the above step (B4-1)) comprising a phospholipid derivative (P-1) or a phospholipid derivative (P-4) predominantly suppresses only expression of GAPDH (without virtually changing the expression amount of Actin) in active-state endothelial cells, that is, exhibited a gene knockdown effect. The gene knockdown effect is higher than that of LFA2K.

Experimental Example B6

Liposome (siRNA) Comprising a Phospholipid Derivative (P-1) or a Phospholipid Derivative (P-4)

Evaluation of gene introduction efficiency (reduction of protein (mTOR) expression) of a liposome comprising a phospholipid derivative (P-1) or a phospholipid derivative (P-4)

B6-1. Preparation of Liposome

Liposome that can be prepared in the above step (B4-1) was used.

B6-2. Cell Culture

As cells, B16BL6 melanoma cells were used. The cells were stored in a DME/HamF12 medium solution (a solution containing 10% fetal bovine serum (FBS) and kanamycin (60 μg/mL)] at 37° C. in the presence of 5% carbon dioxide. Cells, when reached a confluent state, were removed by a 0.25 mg/mL trypsin/EDTA-PBS (−) solution.

B6-3. Evaluation of Gene Knockdown

Twenty four hours before transfection, the cultured cells as mentioned above were placed in a plate having 6 wells. The siRNA solution (Hokkaido System Science Co., Ltd.) capable of knocking down mTOR and the liposome solution prepared in the above step (B4-1) were separately diluted with DEPC treated water and incubated at room temperature for 5 minutes. The siRNA solution was mixed with the liposome solution prepared in the above step (B4-1) in the same volume to obtain a complex containing nitrogen derived from the liposome solution prepared in the above step (B4-1) and phosphorus derived from siRNA in a charge ratio of 24/1. After the complex was incubated at room temperature for 20 minutes, it was added to a cell medium so as to obtain a final siRNA concentration of 50 nM. Four hours after the addition of the complex, the medium was exchanged. Twenty eight hours after the addition of the complex, gene knockdown was evaluated. The culture solution was removed from each of the wells of the plate and the cells were washed once with a PBS solution and lysed by adding 100 μL of a lysis buffer solution [a 1% reduced triton X-100 solution containing 2 mM phenylmethylsulfonyl fluoride (PMSF), 0.2 mM leupeptin, 0.05 mg/mL aprotinin and 0.1 mM pepstatin A]. The cell lysis solution was collected in a 1.5 mL Eppendorf tube, centrifuged at 1000 g for 10 minutes and the supernatant was collected. Each sample was separated by SDS-PAGE. The mTOR amount was detected by the Western blotting method. As a color emitting reagent, ECL Western blotting detection regents (GE Healthcare) were used and detection was carried out by LAS3000 (Fuji Film Corporation).

B6-4. Results

Figure 6:
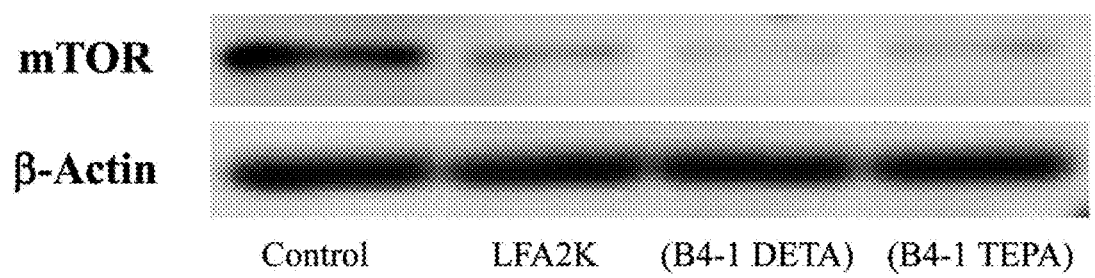
FIG. 6 shows results of gene knockdown evaluation in Experimental Example B6.

The results are shown in FIG. 6.

Gene knockdown was evaluated based on reduction of protein expression as a reference. It is meant that the thinner the band is, the higher the gene knockdown efficiency is.

In FIG. 6, the "(B4-1 DETA)" represents the liposome prepared in the above step (B4-1) using a phospholipid derivative (P-1) and the "(B4-1 TEPA)" represents the liposome prepared in the above step (B4-1) using a phospholipid derivative (P-4).

Each of the Liposome (the above step (B4-1)) comprising a phospholipid derivative (P-1) or a phospholipid derivative (P-4) predominantly suppressed only expression of GAPDH (without virtually changing the expression amount of Actin), that is, exhibited a high gene knockdown effect.

INDUSTRIAL AVAILABILITY

The present invention is directed to phospholipid derivatives useful for producing lipid membrane structures (a liposome, a emulsion and a micelle and the like) having excellent gene/nucleic acid introduction efficiency into a cell.

The phospholipid derivatives of the present invention are useful as lipid membrane structures as a therapeutic carrier and a laboratory reagent that can introduce, e.g., a gene and a nucleic acid having high gene expression efficiency and a high gene expression suppression effect into a cell.

The invention claimed is:

1. A compound represented by the general formula (2) below:

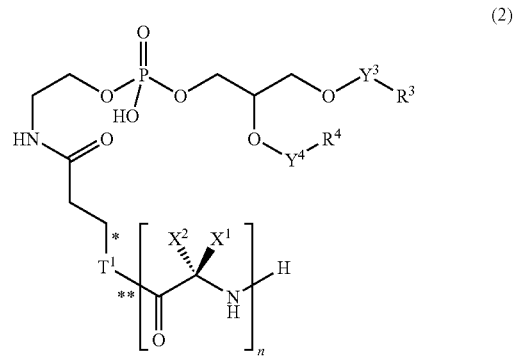

(2)

wherein $R^3$ is an aliphatic hydrocarbon group having 10 to 22 carbon atoms;

$R^4$ is an aliphatic hydrocarbon group having 10 to 22 carbon atoms;

$Y^3$ is a methylene group or a carbonyl group;

$Y^4$ is a methylene group or a carbonyl group;

$X^1$ and $X^2$, which are different from each other, are a hydrogen atom or a group represented by —(CH$_2$)$_3$—NHC(=NH)NH$_2$;

$T^1$ is a group represented by the general formula (T2) or the general formula (T3) below:

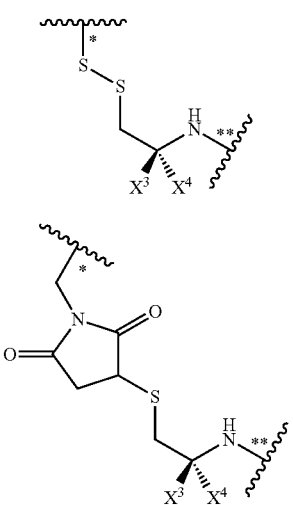

wherein X³ and X⁴, which are different from each other, are a hydrogen atom or a carboxyl group; and n is an integer selected from 4 to 12.

2. The compound according to claim 1, wherein $R^3$ is at least one selected from the group consisting of an undecyl group, a tridecyl group, a pentadecyl group, a heptadecyl and a heptadecenyl group.

3. The compound according to claim 1, wherein $R^4$ is at least one selected from the group consisting of an undecyl group, a tridecyl group, a pentadecyl group, a heptadecyl and a heptadecenyl group.

4. A liposome for introduction of a nucleic acid into a cell comprising:
(a) a nucleic acid; and
(b) a compound represented by the general formula (1) below:

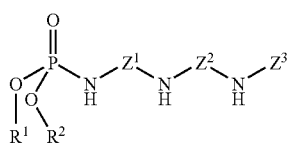

wherein $R^1$ is an aliphatic hydrocarbon group having 10 to 22 carbon atoms;

$R^2$ is an aliphatic hydrocarbon group having 10 to 22 carbon atoms;

$Z^1$ is a C2-4 alkylene group;

$Z^2$ is a C2-3 alkylene group;

$Z^3$ is at least one selected from the group consisting of a hydrogen atom, —$Z^4$—$NH_2$, —$Z^4$—NH—$Z^5$—$NH_2$ and —$((CH_2)_2$—NH$)_q$—H;

$Z^4$ is a C2-4 alkylene group;

$Z^5$ is a C2-4 alkylene group;

q is an integer of 3 to 5;

(c) cholesterol; and (d) at least one phospholipid selected from the group consisting of phosphatidylethanolamine, phosphatidylcholine, phosphatidylserine, phosphatidylinositol, phosphatidylglycerol, cardiolipin, sphingomyelin, ceramide phosphorylethanolamine, ceramide phosphoryl glycerol, ceramide phosphoryl glycerol phosphate, 1,2-dimyristoyl-1,2-deoxyphosphatidylcholine, plasmalogen, phosphatidic acid, dioleoylphosphatidylethanolamine, egg-yolk lecithin and soy-bean lecithin, wherein the liposome is prepared by mixing the formula I compound (b) with cholesterol (c) and phospholipid (d) prior to mixing with the nucleic acid (a).

5. A liposome comprising the compound according to claim 1.

6. The liposome of claim 4, wherein $Z^1$ is —$CH_2$—$CH_2$—.

7. The liposome of claim 4, wherein $Z^2$ is —$CH_2$—$CH_2$—.

8. The liposome of claim 4, wherein $Z^3$ is —$((CH_2)_2$—NH$)_r$—H, wherein r is an integer of 0 to 4.

9. The liposome of claim 4, wherein $R^1$ is at least one selected from the group consisting of a dodecyl group, a tetradecyl group, a hexadecyl group, an octadecyl group and an octadecenyl group.

10. The liposome of claim 4, wherein $R^2$ is at least one selected from the group consisting of a dodecyl group, a tetradecyl group, a hexadecyl group, an octadecyl group and an octadecenyl group.

11. The liposome of claim 4, further comprising at least one compound selected from the group consisting of glucuronic acid derivatives; fatty acids having a saturated or unsaturated acyl group having 8 to 22 carbon atoms; polyethylene glycol derivatives; and antioxidants.

12. The liposome of claim 4, further comprising α-tocopherol.

13. The liposome of claim 4, further comprising distearoylphosphatidylethanolamine.

* * * * *